US012655100B2

(12) United States Patent
Yamada et al.

(10) Patent No.: US 12,655,100 B2
(45) Date of Patent: Jun. 16, 2026

(54) METHOD FOR PRODUCING PYRROLIDINE COMPOUND

(71) Applicant: Takeda Pharmaceutical Limited Company, Osaka (JP)

(72) Inventors: Masatoshi Yamada, Osaka (JP); Sayuri Hirano, Osaka (JP); Osamu Yabe, Osaka (JP); Yuichi Kajita, Osaka (JP); Tsuneo Oda, Kanagawa (JP); Takashi Abe, Kanagawa (JP); Hironori Yamashita, Kanagawa (JP)

(73) Assignee: Takeda Pharmaceutical Limited Company, Osaka (JP)

( * ) Notice: Subject to any disclaimer, the term of this patent is extended or adjusted under 35 U.S.C. 154(b) by 418 days.

(21) Appl. No.: 18/557,255

(22) PCT Filed: Apr. 25, 2022

(86) PCT No.: PCT/IB2022/053829

§ 371 (c)(1),
(2) Date: Oct. 25, 2023

(87) PCT Pub. No.: WO2022/229820

PCT Pub. Date: Nov. 3, 2022

(65) Prior Publication Data

US 2024/0228437 A1 Jul. 11, 2024

(30) Foreign Application Priority Data

Apr. 26, 2021 (JP) ................................ 2021-074435

(51) Int. Cl.
*C07D 207/14* (2006.01)

(52) U.S. Cl.
CPC .................................. *C07D 207/14* (2013.01)

(58) Field of Classification Search
CPC .................................................... C07D 207/14
See application file for complete search history.

(56) References Cited

U.S. PATENT DOCUMENTS 10,428,023 B2 10/2019 Kajita et al.
10,584,097 B2 3/2020 Kajita et al.
11,440,883 B2 9/2022 Kajita et al.
11,655,241 B2 5/2023 Oda et al.
2020/0207734 A1 7/2020 Kajita et al.
2022/0411369 A1 12/2022 Nishiguchi et al.
2023/0063805 A1 3/2023 Kajita et al.

FOREIGN PATENT DOCUMENTS

JP 4-13659 A 1/1992
JP 2002-531558 A 9/2002
JP 2022-371060 A 12/2022
WO WO 1999-50261 A1 7/1999
WO WO 2019-027058 A1 2/2019
WO WO 2020-004537 A1 1/2020
WO WO 2021-100730 A1 5/2021

OTHER PUBLICATIONS

International Search Report and Written Opinion of the International Searching Authority for Appl. No. PCT/IB2022/053829, mailed Jul. 12, 2022, 16 pages.

*Primary Examiner* — Kamal A Saeed
*Assistant Examiner* — Quincy McKoy
(74) *Attorney, Agent, or Firm* — STERNE, KESSLER, GOLDSTEIN & FOX P.L.L.C

(57) ABSTRACT

The present invention provides a method suitable for industrial production of a compound of formula (V): (V) comprising a step of subjecting a compound (IV) to an asymmetric reductive amination reaction in the presence of a metal complex comprising a chiral ligand and subjecting this product to purification using salt formation with N-(4-methylbenzene-1-sulfonyl)-L-phenylalanine. (IV)

(V)

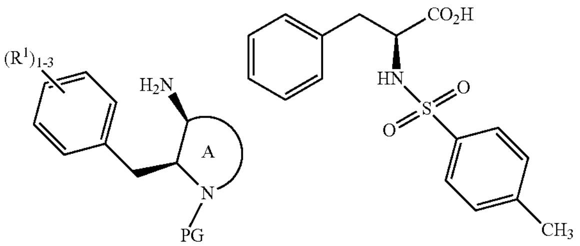

(IV)

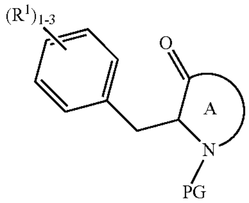

22 Claims, No Drawings

METHOD FOR PRODUCING PYRROLIDINE COMPOUND

TECHNICAL FIELD

The present invention relates to a method for producing a pyrrolidine compound.

BACKGROUND OF THE INVENTION

Pyrrolidine compounds, for example, (2S,3S)-2-[(3-bromo-2-fluorophenyl)methyl]pyrrolidin-3-amine with a protecting group at the 1-position on the pyrrolidine are useful as intermediates in the production of pharmaceuticals, and a method suitable for their industrial production is desired.

In Patent Document 1, compound (18) comprising a 3-oxopyrrolidine ring is subjected to a reductive amination reaction with an iridium catalyst to give the corresponding cis-form compound (19) comprising a 3-aminopyrrolidine ring (Scheme 4). The cis-form is subjected to a chiral column to give the corresponding (2S,3S)-form.

Patent Document 2 discloses a process to obtain (2S,3S) 3-amino-2-(3-bromo-2-fluorobenzyl) pyrrolidine having a protecting group at the 1-position by subjecting 2-(3-bromo-2-fluorobenzyl)-3-(methoxyimino) pyrrolidine having a protecting group at the 1-position to reductive reaction using irconium chloride (IV).

DOCUMENT LIST

Patent Document

Patent Document 1: WO 2019/027058
Patent Document 2: WO 2021/100730

SUMMARY OF THE INVENTION

Problems to be Solved by the Invention

In the method described in Patent Document 1, since the (2S,3S)-form is obtained by optical resolution using a chiral column, it is hard to say that this method is suitable for industrial production. In the method described in Patent Document 2, the purity and yield of (2S,3S) 3-amino-2-(3-bromo-2-fluorobenzyl) pyrrolidine having a protecting group at the 1-position on the pyrrolidine is not sufficient for industrial production.

The object of the present invention is to provide a method suitable for large scale production of chiral (2S,3S)-2-benzyl-3-amino substituted heterocycles. In other aspects, an object of the present invention is to provide a method suitable for industrial production of (2S,3S)-2-[(3-bromo-2-fluorophenyl)methyl]pyrrolidin-3-amine with a protecting group at the 1-position on the pyrrolidine. In other aspects, an object of the present invention is to provide a method suitable for industrial large scale production of N-{(2S,3S)-1-(2-hydroxy-2-methylpropanoyl)-2-[(2,3',5'-trifluoro[1,1'-biphenyl]-3-yl)methyl]pyrrolidin-3-yl}methanesulfonamide using (2S,3S)-2-[(3-bromo-2-fluorophenyl)methyl]pyrrolidin-3-amine with a protecting group at the 1-position on the pyrrolidine to produce.

Means of Solving the Problems

The present inventors have conducted intensive studies to solve the above-mentioned problems, and have found that, by subjecting 2-[(3-bromo-2-fluorophenyl)methyl]pyrrolidin-3-one with a protecting group at the 1-position on the pyrrolidine to an asymmetric reductive amination reaction in the presence of a metal complex comprising a chiral ligand, and then by subjecting the resulting compound to purification using salt formation with a specific chiral acid, (2S,3S)-2-[(3-bromo-2-fluorophenyl)methyl]pyrrolidin-3-amine with a protecting group at the 1-position on the pyrrolidine can be obtained as a salt; and have also found that the raw material 2-[(3-bromo-2-fluorophenyl)methyl]pyrrolidin-3-one with a protecting group at the 1-position on the pyrrolidine can be obtained with higher purity, and completed the present invention based on these findings.

Accordingly, the present invention provides the following.

[1]

A method for producing a compound of formula (V):

(V)

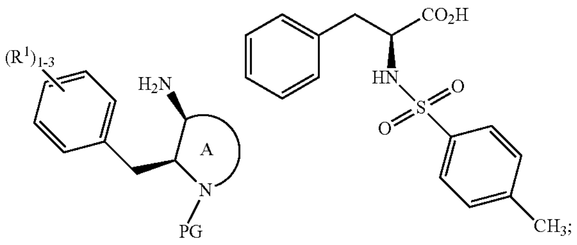

wherein each $R^1$ is independently selected from a halogen atom and a trifluoromethanesulfonyl group;

A is an optionally further substituted 4-7 membered N-containing monocyclic saturated heterocyclyl; and PG is a protecting group, the process comprising subjecting a compound of formula (IV):

(IV)

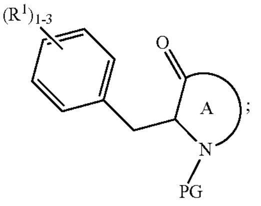

to an asymmetric reductive amination reaction in the presence of a metal complex comprising a chiral ligand and subjecting the resulting product to purification using salt formation with N-(4-methylbenzene-1-sulfonyl)-L-phenylalanine.

[2]

The method according to the above-mentioned [1], further comprising:

(a) reacting a compound of formula (II):

(II)

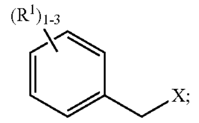

wherein $R^1$ is independently selected from a halogen atom and a trifluoromethanesulfonyl group; and X is a halogen atom, with an anion of a compound of formula (III):

III)

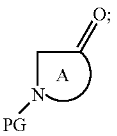

wherein

PG is a protecting group; and

A is an optionally further substituted 4-7 membered N-containing monocyclic saturated heterocycle;

(b) deprotecting the product of step (a);

(c) reacting the product of step (b) with a racemate of an organic acid; and (d) introducing a protecting group to the product of step (c); to provide the compound of formula (IV).

[3]

The method according to the above-mentioned [1] or [2], wherein A is selected from pyrrolidine, piperidine, and azetidine, each of which is optionally further substituted.

[4] The process according to any of the above-mentioned [1] to [3], where in A is pyrrolidine.

[5]

The method according to any of the above-mentioned [1] to [4], wherein each $R^1$ is independently selected from Cl, Br, I, and a trifluoromethanesulfonyl group.

[6]

The method according to any of the above-mentioned [2] to [5], wherein the organic acid is racemic tartaric acid (DL-tartaric acid).

[7]

A method for producing N-(4-methylbenzene-1-sulfonyl)-L-phenylalanine salt of (2S,3S)-2-[(3-bromo-2-fluorophenyl)methyl]pyrrolidin-3-amine with a protecting group at the 1-position on the pyrrolidine (hereinafter also referred to as compound (5)), which comprises a step comprising Step 3a: subjecting 2-[(3-bromo-2-fluorophenyl)methyl]pyrrolidin-3-one with a protecting group at the 1-position on the pyrrolidine (hereinafter also referred to as compound (4)) to an asymmetric reductive amination reaction in the presence of a metal complex comprising a chiral ligand; and Step 3b: subjecting the product of Step 3a to purification using salt formation with N-(4-methylbenzene-1-sulfonyl)-L-phenylalanine.

[8]

The method according to the above-mentioned [7], further comprising

Step 1a: reacting 1-bromo-3-(bromomethyl)-2-fluorobenzene with pyrrolidin-3-one with a protecting group at the 1-position on the pyrrolidine;

Step 1b: deprotecting the product of Step 1a and reacting with DL-tartaric acid; and Step 2: introducing a protecting group to the product of Step 1b to provide 2-[(3-bromo-2-fluorophenyl)methyl]pyrrolidin-3-one with a protecting group at the 1-position on the pyrrolidine.

[9]

The method according to any of the above-mentioned [1] to [8], wherein the chiral ligand in the metal complex is a BINAP ligand, a phosphine ligand, a ferrocene ligand, or a cyclophane ligand.

[10]

The method according to any of the above-mentioned [1] to [8], wherein the metal in the metal complex is ruthenium, rhodium, or iridium.

[11]

The method according to any of the above-mentioned [1] to [8], wherein the metal complex comprising a chiral ligand is a ruthenium complex comprising a chiral BINAP ligand, or a ruthenium complex comprising a chiral cyclophane ligand.

[12]

The method according to any of the above-mentioned [1] to [8], wherein the metal complex comprising a chiral ligand is a metal complex represented by the formula:

$$Ru(OAc)_2(Ligand)$$

wherein Ligand is (S)-binap, (R)-xylyl-Phanephos or (R)-xylyl-binap.

[13]

The method according to any of the above-mentioned [1] to [8], wherein the metal complex comprising a chiral ligand is $Ru(OAc)_2\{(R)\text{-xylyl-binap}\}$.

[14]

The method according to any of the above-mentioned [1] to [13], wherein the protecting group at the 1-position on the pyrrolidine is selected from tert-butoxycarbonyl, benzyloxycarbonyl, acetyl, trityl, benzyl, 9-fluorenylmethyloxycarbonyl, 2,2,2-trichloroethoxycarbonyl, and methoxymethyl.

[15]

The method according to any of the above-mentioned [1] to [14], wherein the protecting group at the 1-position on the pyrrolidine is a tert-butoxycarbonyl group.

[16]

The method according to any one of the above-mentioned [1] to [15], wherein the purification conditions comprises crystallization.

[17]

The method according to the above-mentioned [16], wherein the crystallization comprises a salt formation with N-(4-methylbenzene-1-sulfonyl)-L-phenylalanine, which is conducted in a solvent at a temperature from 60° C. to 78° C., stirring at a temperature from 60° C. to 78° C. for about 0.5 hours, stirring at 15° C. to 35° C. for about 12 to about 48 hours, and filtering the resulting precipitate.

[18]

The method according to the above-mentioned [17], further comprising recrystallizing the precipitate from a solvent selected from an alcohol, ether, and an aromatic hydrocarbon.

[19]

The method according to the above-mentioned [18], wherein the solvent is ethanol.

[20]

The method according to the above-mentioned [7] or [8], further comprising:

Step 4: subjecting the N-(4-methylbenzene-1-sulfonyl)-L-phenylalanine salt of (2S,3S)-2-[(3-bromo-2-fluorophenyl)methyl]pyrrolidin-3-amine with a protecting group at the 1-position on the pyrrolidine to desalination and reacting with a methanesulfonylating agent;

Step 5: reacting the product of Step 4 with (3,5-difluorophenyl) boronic acid;

Step 6: subjecting the product of Step 5 to deprotection conditions; and

Step 7: subjecting the product of Step 6 to a condensation reaction with 2-hydroxy-2-methylpropanoic acid to give N-{(2S,3S)-1-(2-hydroxy-2-methylpropanoyl)-2-[(2,3',5'-trifluoro[1,1'-biphenyl]-3-yl)methyl]pyrrolidin-3-yl}methanesulfonamide, or a hydrate thereof, or a solvate thereof.

[21]

A compound which is a racemic organic acid salt of

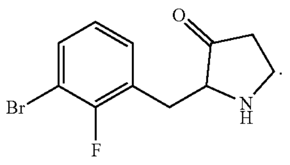 [SMILES: O=C1CCNC1Cc1cccc(Br)c1F]

[22]

The compound according to the above-mentioned [21], which is a racemic tartaric acid salt.

[23]

The compound according to the above-mentioned, which is

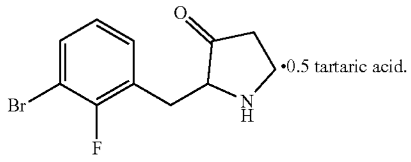 [SMILES: O=C1CCNC1Cc1cccc(Br)c1F]

[24]

A method for producing 2-[(3-bromo-2-fluorophenyl) methyl]pyrrolidin-3-one (hereinafter also referred to as compound (3)) hemi-tartrate, which comprises a step comprising Step 1a: reacting 1-bromo-3-(bromomethyl)-2-fluorobenzene (hereinafter also referred to as compound (1)) and pyrrolidin-3-one with a protecting group at the 1-position on the pyrrolidine (hereinafter also referred to as compound (2)), and Step 1b: subjecting the product of Step 1a to a deprotection reaction, followed by salt formation with tartaric acid.

[25]

A method for producing 2-[(3-bromo-2-fluorophenyl) methyl]pyrrolidin-3-one with a protecting group at the 1-position on the pyrrolidine, which comprises Step 2: a step of introducing a protecting group into the 1-position on the pyrrolidine of 2-[(3-bromo-2-fluorophenyl)methyl]pyrrolidin-3-one hemi-tartrate.

[26]

2-[(3-Bromo-2-fluorophenyl)methyl]pyrrolidin-3-one hemitartrate.

[27]

A method for producing N-{(2S,3S)-1-(2-hydroxy-2-methylpropanoyl)-2-[(2,3',5'-trifluoro[1,1'-biphenyl]-3-yl) methyl]pyrrolidin-3-yl}methanesulfonamide, or a hydrate thereof, or a solvate thereof, which comprises a step comprising Step 1a: reacting 1-bromo-3-(bromomethyl)-2-fluorobenzene with pyrrolidin-3-one with a protecting group at the 1-position on the pyrrolidine, and Step 1b: subjecting the product of Step 1a to a deprotection reaction, followed by salt formation with tartaric acid, to give 2-[(3-bromo-2-fluorophenyl)methyl]pyrrolidin-3-one hemi-tartrate;

Step 2: a step of introducing a protecting group into the 1-position on the pyrrolidine of 2-[(3-bromo-2-fluorophenyl)methyl]pyrrolidin-3-one hemi-tartrate to give 2-[(3-bromo-2-fluorophenyl)methyl]pyrrolidin-3-one with a protecting group at the 1-position on the pyrrolidine;

a step comprising

Step 3a: subjecting 2-[(3-bromo-2-fluorophenyl)methyl] pyrrolidin-3-one with a protecting group at the 1-position on the pyrrolidine to an asymmetric reductive amination reaction in the presence of a metal complex comprising a chiral ligand, and Step 3b: subjecting the product of Step 3a to purification using salt formation with N-(4-methylbenzene-1-sulfonyl)-L-phenylalanine, to give N-(4-methylbenzene-1-sulfonyl)-L-phenylalanine salt of (2S,3S)-2-[(3-bromo-2-fluorophenyl)methyl] pyrrolidin-3-amine with a protecting group at the 1-position on the pyrrolidine;

Step 4: a step of subjecting N-(4-methylbenzene-1-sulfonyl)-L-phenylalanine salt of (2S,3S)-2-[(3-bromo-2-fluorophenyl)methyl]pyrrolidin-3-amine with a protecting group at the 1-position on the pyrrolidine to desalination, and then reacting the resulting compound with a methanesulfonylating agent to give N-(2S,3S)-2-[(3-bromo-2-fluorophenyl)methyl]pyrrolidin-3-yl) methanesulfonamide with a protecting group at the 1-position on the pyrrolidine (hereinafter also referred to as compound (6));

Step 5: a step of reacting N-(2S,3S)-2-[(3-bromo-2-fluorophenyl)methyl]pyrrolidin-3-yl) methanesulfonamide with a protecting group at the 1-position on the pyrrolidine with (3,5-difluorophenyl) boronic acid to give N-{(2S,3S)-2-[(2,3',5'-trifluoro[1,1'-biphenyl]-3-yl) methyl]pyrrolidin-3-yl}methanesulfonamide with a protecting group at the 1-position on the pyrrolidine (hereinafter also referred to as compound (7));

Step 6: a step of subjecting N-{(2S,3S)-2-[(2,3',5'-trifluoro[1,1'-biphenyl]-3-yl)methyl]pyrrolidin-3-yl}methanesulfonamide with a protecting group at the 1-position on the pyrrolidine to a deprotection reaction to give N-{(2S,3S)-2-[(2,3',5'-trifluoro[1,1'-biphenyl]-3-yl)methyl]pyrrolidin-3-yl}methanesulfonamide (hereinafter also referred to as compound (8)) hydrochloride; and Step 7: a step of subjecting N-{(2S,3S)-2-[(2,3',5'-trifluoro[1,1'-biphenyl]-3-yl)methyl]pyrrolidin-3-yl}methanesulfonamide hydrochloride to a condensation reaction with 2-hydroxy-2-methylpropanoic acid to give N-{(2S,3S)-1-(2-hydroxy-2-methylpropanoyl)-2-[(2,3',5'-trifluoro[1,1'-biphenyl]-3-yl)methyl]pyrrolidin-3-yl}methanesulfonamide, or a hydrate thereof, or a solvate thereof (hereinafter also referred to as compound (I)).

[28]

The method according to the above-mentioned, wherein the metal complex comprising a chiral ligand in Step 3a is $Ru(OAc)_2${(R)-xylyl-binap}.

[29]

The method according to the above-mentioned [27], which further comprises a step of isolating 2-[(3-bromo-2-fluorophenyl)methyl]pyrrolidin-3-one hemi-tartrate produced in Step 1b.

[30]

The method according to the above-mentioned, wherein wherein the protecting group at the 1-position on the pyrrolidine is selected from tert-butoxycarbonyl, benzyloxycarbonyl, acetyl, trityl, benzyl, 9-fluorenylmethyloxycarbonyl, 2,2,2-trichloroethoxycarbonyl, and methoxymethyl.

[31]

The method according to any of the above-mentioned to, wherein the protecting group at the 1-position on the pyrrolidine is a tert-butoxycarbonyl group.

[32]

A compound of formula (V):

(V)

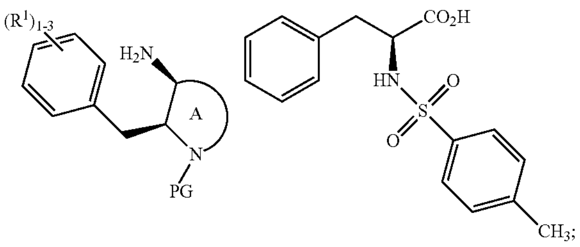

wherein each $R^1$ is independently selected from a halogen atom and a trifluoromethanesulfonyl group;

A is an optionally further substituted 4-7 membered N-containing monocyclic saturated heterocyclyl; and PG is a protecting group, which is prepared by a process comprising subjecting a compound of formula (IV):

(IV)

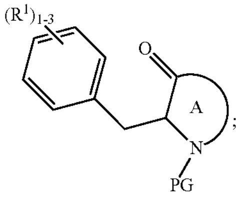

to an asymmetric reductive amination reaction in the presence of a metal complex comprising a chiral ligand and subjecting the resulting product to purification using salt formation with N-(4-methylbenzene-1-sulfonyl)-L-phenylalanine.

[33]

Tert-butyl (2S,3S)-3-amino-2-[(3-bromo-2-fluorophenyl)methyl]pyrrolidine-1-carboxylate N-(4-methylbenzene-1-sulfonyl)-L-phenylalanine salt, which is prepared by subjecting tert-butyl 2-[(3-bromo-2-fluorophenyl)methyl]-3-oxopyrrolidine-1-carboxylate to an asymmetric reductive amination reaction in the presence of $Ru(OAc)_2${(R)-xylyl-binap}; and subjecting the resulting product to purification using salt formation with N-(4-methylbenzene-1-sulfonyl)-L-phenylalanine.

Effect of the Invention

According to the production method of the present invention, compound (5) can be obtained as N-(4-methylbenzene-1-sulfonyl)-L-phenylalanine salt by a method suitable for industrial production.

DETAILED DESCRIPTION OF THE INVENTION

The production method of the present invention is explained below.

The compound obtained in each step can be used directly as the reaction mixture or as a crude product for the next reaction. Alternatively, the compound obtained in each step can be isolated and purified from a reaction mixture according to a method known per se, for example, separation means such as concentration, crystallization, recrystallization, distillation, solvent extraction, fractional distillation, column chromatography and the like. “Treat”, “treated” or “treating” used in the production method of the present invention is synonymous with the term “react” “reacted” or “reacting”.

When the raw material compound and reagent used in each step are commercially available, the commercially available product can also be used directly.

Unless otherwise specified, the reaction in each step is carried out without solvent, or by dissolving or suspending the raw material compound in a suitable solvent. Examples of the solvent include those described in the Examples and the following solvents:

alcohols: methanol, ethanol, tert-butyl alcohol, 2-methoxyethanol, 1-propanol, 2-propanol and the like;

ethers: diethyl ether, diisopropyl ether, cyclopentyl methyl ether (CPME), diphenyl ether, tetrahydrofuran (THF), 1,2-dimethoxyethane, 1,4-dioxane, and the like;

aromatic hydrocarbons: chlorobenzene, toluene, xylene and the like;

saturated hydrocarbons: cyclohexane, hexane and the like;

amides: N,N-dimethylformamide, N,N-dimethylacetamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

organic bases: pyridine, triethylamine and the like;

acid anhydrides: acetic anhydride and the like;

organic acids: formic acid, acetic acid, trifluoroacetic acid and the like;

inorganic acids: hydrochloric acid, sulfuric acid and the like;

esters: ethyl acetate, isopropyl acetate and the like;

ketones: acetone, methyl ethyl ketone and the like;

water.

The above-mentioned solvent can be used in a mixture of two or more kinds thereof in an appropriate ratio.

When a base is used for the reaction in each step, examples thereof include the following bases and those described in the Examples.

inorganic bases: sodium hydroxide, magnesium hydroxide, sodium carbonate, calcium carbonate, sodium hydrogencarbonate, potassium carbonate, sodium acetate, lithium hydroxide, tripotassium phosphate and the like;

organic bases: triethylamine, diethylamine, diisopropylethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, pyrrolidine and the like;

metal alkoxides: sodium methoxide, sodium ethoxide, potassium tert-butoxide, sodium tert-butoxide, lithium ethoxide and the like;

alkali metal hydrides: sodium hydride and the like;

metal amides: sodium amide, lithium diisopropylamide, lithium hexamethyldisilazide and the like;

organic lithiums: n-butyllithium and the like.

In the present invention, compounds of formula (V) can be produced from compounds of formula (II), and the compounds of formula (V) can be used in the preparation of compounds of formula (X), as shown in Scheme 1 (herein after, compounds of formula ( . . . ) may be simply referred as “compound ( . . . )”).

Scheme 1

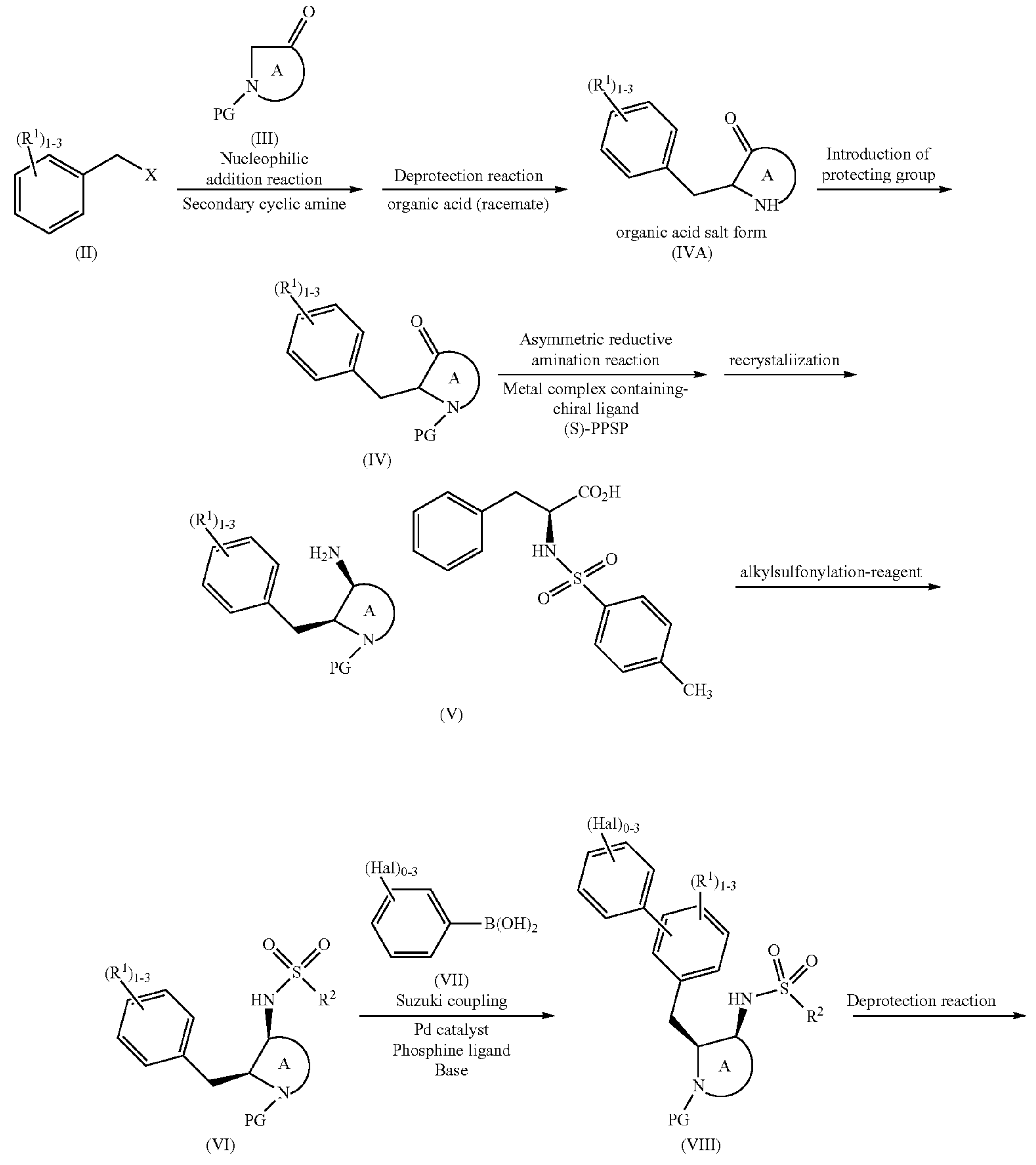

-continued

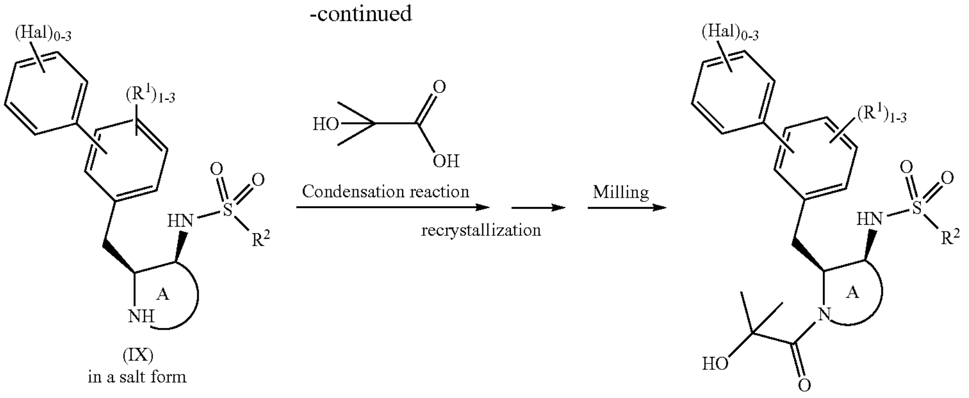

(IX)
in a salt form (X)
as hydrate, anhydrate, or solvate

Compound (II) (X is a halogen atom or a trifluoromethane sulfonate group) can be reacted with a compound (III) (A is an optionally further substituted 4- to 7-membered nitrogen containing monocyclic saturated heterocycle. Examples of A include pyrrolidine, piperidine, and azetidine, each of which is optionally further substituted. Preferable examples of A include pyrrolidine, piperidine, and azetidine, and more preferable example of A is pyrrolidine.) by nucleophilic substitution of group X with a carbanion of compound (III). Examples of the base to be used for generation of the carbanion include organic lithiums, metal alkoxides, inorganic bases, organic bases, and the like. In certain aspects, the base can be an organic base. In some aspects, the base can be a secondary amine. In some aspects, the base can be pyrrolidine.

Removal of the protecting group using conditions appropriate for the chosen protecting group followed by reaction with an acid provides compound (IVA) as a salt form. In addition to an organic acid (including an organic acid racemate), an inorganic acid (i.e. HCl) may be used for the purpose of crystallization of compound (IVA).

Examples of organic acids include formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Examples of inorganic acids include hydrochloric acid, hydrobromic acid, nitric acid, sulfuric acid, phosphoric acid and the like.

In certain aspects, the compound of formula (IVA) is formed as a salt of an organic acid racemate. In some aspects, the organic salt is the racemate of tartaric acid (DL-tartaric acid).

The compound of formula (IVA) can be protected with an appropriate protecting group to provide a compound of formula (IV).

Asymmetric reductive amination in the presence of a metal complex containing-chiral ligand, as described further herein, provides compound (V). Examples of the metal catalyst to be used catalyst such as $Ru(OAc)_2$\{(R)-binap\}, include Ru [RuCl2(benzene)]2 and Ru(OAc)2\{(R\}-xylyl-binap\}, and Rh catalyst such as [RhCl(cod)]2 and [Rh (cod) 2]OTf, and examples of ligand to be used include (S)-binap, (R)-xylyl-phanephos and (R)-xylyl-binap, and examples of hydrogen source to be used include hydrogen gas, formic acid, ammonium formate and the like. In addition, nitrogen source can be added to the reaction system, and examples thereof include ammonia and ammonium acetate and the like.

Reacting compound (V) with a an alkylsulfonylation reagent (e.g. methanesulfonylation agent, ethanesulfonylation reagent) provides compound (VI) ($R^2$ is $C_{1-2}$ alkyl) which can be further coupled with (VII) to provide compound (VIII) by Suzuki coupling (Suzuki-Miyaura coupling). Examples of the metal catalyst to be used in the coupling include palladium compounds such as palladium (II) acetate, tetrakis(triphenylphosphine)palladium (0), dichlorobis(triphenylphosphine)palladium (II), dichlorobis (triethylphosphine)palladium (II), tris(dibenzyl-ideneacetone)dipalladium (0), 1,1'-bis(diphenylphosphino)-ferrocene palladium (II) chloride and the like; nickel compounds such as tetrakis(triphenylphosphine) nickel (0) and the like; rhodium compounds such as tris(triphenylphosphine) rhodium (III) chloride and the like; cobalt compounds; copper compounds such as copper oxide, copper (I) iodide and the like; platinum compounds and the like. In addition, a base can be added to the reaction system, and examples thereof include inorganic bases and the like.

Deprotection of compound (VIII) provides compound (IX) in a salt form. Examples of the salt include hydrochloride and tartaric acid and the like, and preferably the salt is hydrochoride. Compound (IX) can be reacted with 2-hydroxy-2-methylpropanoic acid to provide compound (X) in a form of hydrate, anhydrate, or solvate. A hydrate includes hemihydrate and sesqui-hydrate.

In the various pyrrolidine compounds used as raw materials or products in the production method of the present invention, examples of the protecting group for the 1-position of the pyrrolidine include a tert-butoxycarbonyl group, a benzyloxycarbonyl group, an acetyl group, a trityl group, a benzyl group, a 9-fluorenylmethyloxycarbonyl group (Fmoc group), a 2,2,2-trichloroethoxycarbonyl group (Troc group), a methoxymethyl group (MOM group) and the like, and the preferred is a tert-butoxycarbonyl group in terms of easy deprotection. In the present specification, examples of the “optionally further substituted 4-7 membered N-containing monocyclic saturated heterocyclyl” include a heterocyclyl optionally having 1 to 3 substituent (s) selected from a halogen atom, a nitro group, a cyano group, a hydroxy group, an optionally halogenated $C_{1-6}$ alkoxy group, a carboxy group, an optionally halogenated $C_{1-6}$ alkyl group, a carbamoyl group, an amino group, a $C_{2-6}$ alkenyl group, a $C_{2-6}$ alkynyl group, and a $C_{3-10}$ cycloalkyl group.

In the present invention, N-(4-methylbenzene-1-sulfonyl)-L-phenylalanine salt of compound (5) can be produced by a step comprising the following Step 3a and Step 3b.

Step 3a: subjecting compound (4) to an asymmetric reductive amination reaction in the presence of a metal complex comprising a chiral ligand; and Step 3b: subjecting the product of Step 3a to purification using salt formation with N-(4-methylbenzene-1-sulfonyl)-L-phenylalanine.

Step 3a

In this step, compound (4) is subjected to an asymmetric reductive amination reaction in the presence of a metal complex comprising a chiral ligand.

The reaction is carried out by reacting compound (4) with an amine source under hydrogen atmosphere in the presence of a metal complex comprising a chiral ligand, in a solvent.

Compound (4) is preferably tert-butyl 2-[(3-bromo-2-fluorophenyl)methyl]-3-oxopyrrolidine-1-carboxylate (compound (4a)). The compound can be produced by a method known per se. Alternatively, the compound can also be produced by a step comprising Step 1a and Step 1b, and Step 2, as mentioned below.

Examples of the amine source include ammonia, ammonium salts such as ammonium chloride, ammonium formate, ammonium acetate, ammonium salicylate and the like, and the like. Among them, the preferred is combination of ammonium chloride and ammonium acetate.

The amount of the amine source to be used is generally 2 to 8 mol, preferably 4 to 6 mol, per 1 mol of compound (4).

Examples of the chiral ligand in the metal complex comprising a chiral ligand include BINAP ligands such as (S)-BINAP, (R)-Xylyl-BINAP, (R)-p-tol-BINAP, (S)-m-tol-BINAP, (S)-DMANYL-BINAP, (S)-DADMP-BINAP, (R)-H8-BINAP, (S)-PMP-BINAP, (S)-BOP-BINAP and the like; phosphine ligands such as (R,R)-iPr-DUPHOS, (R)-SYNPHOS, (R)-SOLPHOS, (R)-MeO-BIPHEP, (R)-ClMeO-BIPHEP, (R,R)-Skewphos, (R,R)-PTBP-Skewphos, (R)-MONOPHOS and the like; ferrocene ligands such as (R) (S)-SL-J003, (R) (R)-SL-T001, (R) (R)-SL-W002, (R) (S)-JOSIPHOS and the like; cyclophane ligands such as (R)-PHANEPHOS, (R)-Xylyl-PHANEPHOS and the like, and the like.

Among them, in terms of enantioselectivity, amine selectivity and cis selectivity, it is preferably a BINAP ligand such as (S)-BINAP, (R)-Xylyl-BINAP, (R)-p-tol-BINAP, (S)-m-tol-BINAP, (S)-DMANYL-BINAP, (S)-DADMP-BINAP, (R)-H8-BINAP, (S)-PMP-BINAP, (S)-BOP-BINAP and the like, or a cyclophane ligand such as (R)-PHANEPHOS, (R)-Xylyl-PHANEPHOS and the like, more preferably (S)-BINAP, (R)-p-tol-BINAP, (S)-m-tol-BINAP, (R)-Xylyl-PHANEPHOS or (R)-Xylyl-BINAP, still more preferably (S)-BINAP, (R)-Xylyl-PHANEPHOS or (R)-Xylyl-BINAP, particularly preferably (R)-Xylyl-BINAP.

In terms of enantioselectivity and cis selectivity, the metal in metal complex comprising a chiral ligand is preferably ruthenium, rhodium or iridium, particularly preferably ruthenium.

Examples of such metal complex comprising a chiral ligand include a ruthenium complex comprising a chiral BINAP ligand, and a ruthenium complex comprising a chiral cyclophane ligand.

Preferable specific examples thereof include metal complexes having the structure selected from the following formulas (Ia) to (Id).

(Ia)

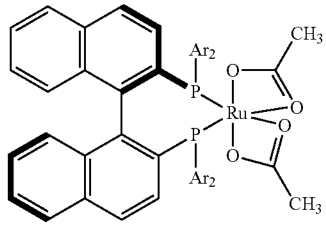

(Ib)

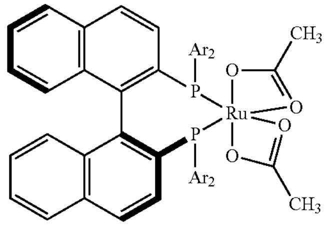

(Ic)

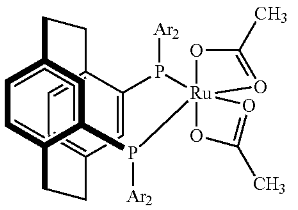

(Id)

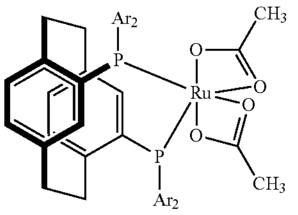

wherein Ar is phenyl, tolyl or xylyl.

The metal complex comprising a chiral ligand is more preferably a metal complex represented by the formula:

$Ru(OAc)_2$ (Ligand)

wherein Ligand is (S)-binap, (R)-xylyl-Phanephos or (R)-xylyl-binap.

Ligand is preferably (R)-xylyl-binap.

The metal complex comprising a chiral ligand is particularly preferably $Ru(OAc)_2$\{(R)-xylyl-binap\}.

The amount of the metal complex comprising a chiral ligand to be used is generally 0.10 to 1.00 mol %, preferably 0.40 to 0.60 mol %, per 1 mol of compound (4).

The hydrogen pressure is generally 0.60 to 5.00 MPa (G), preferably 0.80 to 1.00 MPa (G).

Examples of the solvent include alcohols; ethers; water and the like. Among them, the preferred are methanol, and a mixed solvent of methanol and water.

The reaction is carried out generally at 75 to 95° C., preferably at 80 to 85° C. The reaction time is generally about 10 hr to about 72 hr, preferably about 16 hr to about 48 hr.

After completion of the reaction, conventional workup such as phase separation, concentration and the like is performed.

In the reaction, it is desirable that the conversion rate of compound (4) is 95% or more, particularly 99% or more.

The reaction also yields 2-[(3-bromo-2-fluorophenyl)methyl]pyrrolidin-3-ol with a protecting group at the 1-position on the pyrrolidine as a by-product. However, it is desirable that 2-[(3-bromo-2-fluorophenyl)methyl]pyrrolidin-3-amine with a protecting group at the 1-position on the pyrrolidine (hereinafter also referred to as compound (5A)) is produced with amine selectivity of 80% or more, particularly 90% or more.

The reaction also yields the trans-form ((2R,3S) and (2S,3R)), in addition to the cis-form ((2S,3S) and (2R,3R)). However, it is desirable that the cis-form of compound (5A) with a protecting group at the 1-position on the pyrrolidine is produced in yield of 50% or more, particularly 70% or more.

In the reaction, it is desirable that compound (5) is produced with enantiomeric excess of 25% or more, particularly 35% or more.

Compound (5) present in the product obtained in this step is obtained as a N-(4-methylbenzene-1-sulfonyl)-L-phenylalanine salt in the next Step 3b.

Step 3b

In this step, N-(4-methylbenzene-1-sulfonyl)-L-phenylalanine salt of compound (5) can be obtained by subjecting the product of Step 3a to purification using salt formation with N-(4-methylbenzene-1-sulfonyl)-L-phenylalanine.

The purification is carried out by mixing the product of Step 3a with N-(4-methylbenzene-1-sulfonyl)-L-phenylalanine in a solvent, and then collecting the precipitated crystals by filtration.

The amount of the N-(4-methylbenzene-1-sulfonyl)-L-phenylalanine to be used is generally 1.1 to 2.4 mol, preferably 1.2 to 2.2 mol, per 1 mol of compound (5) contained in the product of Step 3a. In addition, the amount of the N-(4-methylbenzene-1-sulfonyl)-L-phenylalanine to be used is generally 0.80 to 1.20 mol, preferably 0.90 to 1.10 mol, based on compound (4) which is the starting material for Step 3a.

Examples of the solvent for mixing the product of Step 3a with N-(4-methylbenzene-1-sulfonyl)-L-phenylalanine include alcohols, ethers, aromatic hydrocarbons and the like. Among them, the preferred is ethanol.

The mixing is carried out by adding (preferably adding dropwise), under stirring, a solution of the product of Step 3a to N-(4-methylbenzene-1-sulfonyl)-L-phenylalanine. The mixing is also carried out by adding N-(4-methylbenzene-1-sulfonyl)-L-phenylalanine, under stirring, to a solution of the product of Step 3a. The addition temperature is generally 60 to 78° C., preferably 65 to 75° C. After the addition, the mixture is aged under stirring generally at 60 to 78° C., preferably at 65 to 75° C. for about 0.5 hr, and then at 15 to 35° C., preferably at 20 to 30° C. for about 12 hr to about 48 hr, preferably for about 18 hr to about 24 hr.

By the above operations, crystals of N-(4-methylbenzene-1-sulfonyl)-L-phenylalanine salt of compound (5) are precipitated. The precipitated crystals are collected by filtration, and then, if necessary, recrystallized from a solvent such as alcohols, ethers, aromatic hydrocarbons and the like. Among such solvent, the preferred is ethanol.

Thus, N-(4-methylbenzene-1-sulfonyl)-L-phenylalanine salt of compound (5) can be obtained with high purity (e.g., purity of 98.5% or more).

The purity of compound (4) which is the starting material for Step 3a greatly affects the purity of N-(4-methylbenzene-1-sulfonyl)-L-phenylalanine salt of compound (5). Therefore, in order to obtain N-(4-methylbenzene-1-sulfonyl)-L-phenylalanine salt of compound (5) with higher purity, it is important to use compound (4) with higher purity in Step 3a.

When compound (4) is tert-butyl 2-[(3-bromo-2-fluorophenyl)methyl]-3-oxopyrrolidine-1-carboxylate (compound (4a)), this compound is hard to be crystallized. Therefore, it has been difficult to increase the purity.

The inventors succeeded in obtaining compound (4) with higher purity by a step comprising the following Step 1a and Step 1b, and the following Step 2.

A step comprising

Step 1a: reacting compound (1) and compound (2), and

Step 1b: subjecting the product of Step 1a to a deprotection reaction, followed by salt formation with tartaric acid, to give hemi-tartrate of compound (3); and Step 2: a step of introducing a protecting group into the 1-position on the pyrrolidine of hemi-tartrate of compound (3) to give compound (4).

Step 1a

In this step, compound (1) and compound (2) are reacted.

The reaction is carried out by reacting compound (1) and compound (2) in the presence of a secondary amine in a solvent. In more detail, the reaction is carried out by converting compound (2) to the activated form (enamine form) in the presence of a secondary amine in a solvent, and then reacting the activated form with compound (1).

Compound (1) may be a commercially available product.

Compound (2) is preferably tert-butyl 3-oxopyrrolidine-1-carboxylate compound (2a)), and may be a commercially available product.

The amount of compound (2) to be used is generally 1.5 to 2.5 mol, preferably 1.9 to 2.1 mol, per 1 mol of compound (1).

Examples of the secondary amine include cyclic amines. Among them, the preferred is pyrrolidine.

The amount of the secondary amine to be used is generally 1.5 to 3.5 mol, preferably 2.0 to 3.0 mol, per 1 mol of compound (1).

If necessary, a phase transfer catalyst such as tetrabutylammonium iodide (TBAI) and the like may be added to the reaction system. The amount thereof to be used is generally 0.01 to 0.20 mol, preferably 0.09 to 0.11 mol, per 1 mol of compound (1).

Examples of the solvent include aromatic hydrocarbons, nitriles and the like. Among them, the preferred is a mixed solvent of toluene and acetonitrile.

The reaction is carried out generally at 20 to 55° C., preferably at 35 to 45° C. The reaction time is generally about 30 min to about 12 hr, preferably about 1 hr to about 2 hr.

After completion of the reaction, conventional workup such as phase separation, concentration and the like is performed.

The reaction yields compound (4), which can be subjected to the next Step 1b without isolation from the reaction mixture.

Step 1b

In this step, hemi-tartrate of compound (3) can be obtained by subjecting the product of Step 1a to a deprotection reaction, followed by salt formation with tartaric acid.

The deprotection reaction depends on the kind of the protecting group at the 1-position on the pyrrolidine. For example, when the protecting group is a tert-butoxycarbonyl group, the deprotection reaction is carried out by reacting with an acid in a solvent.

Examples of the acid include hydrogen chloride and the like. Hydrogen chloride is used preferably as a solution in an organic solvent, particularly preferably as a solution of hydrogen chloride in 2-propanol.

Examples of the solvent include alcohols, esters and the like. Among them, the preferred are 2-propanol, ethyl acetate and mixed solvents thereof, the particularly preferred is 2-propanol.

The reaction is carried out generally at 40 to 60° C., preferably at 45 to 55° C. The reaction time is generally about 1 hr to about 6 hr, preferably about 2 hr to about 4 hr.

The reaction yields compound (3), which precipitates as a hydrochloride when the deprotection reaction is treated with hydrogen chloride. After completion of the reaction, the hydrochloride can be obtained by adding ethyl acetate at 45 to 55° C. for crystallization, and cooling to 0 to 10° C. over 1 hr or longer, and then washing with ethyl acetate. The obtained hydrochloride of compound (3) is converted to the free form by adding a base in a solvent, and subjected to the next salt formation with tartaric acid.

The salt formation with tartaric acid is carried out by mixing compound (3) and tartaric acid in a solvent, and then collected the resulting precipitated crystals by filtration.

The amount of tartaric acid to be used is generally 0.3 to 1.0 mol, preferably 0.4 to 0.6 mol, per 1 mol of compound (1).

Examples of the solvent include alcohols; aromatic hydrocarbons; ketones and the like. Among them, the preferred is a mixed solvent of methanol and toluene.

The mixing is carried out by adding (preferably adding dropwise), under stirring, a solution of compound (3) to a solution of tartaric acid. The addition temperature is generally 15 to 35° C., preferably 20 to 30° C. After the addition, the mixture is aged under stirring generally at −5 to 15° C., preferably at 0 to 10° C. for about 1 hr to about 24 hr.

By the above operations, crystals of hemi-tartrate of compound (3) are precipitated. The crystals of hemi-tartrate of compound (3) can be obtained by collecting the precipitated crystals by filtration, washing with a mixed solvent of methanol and toluene, and then drying.

In order to obtain compound (4) to be used in Step 3a with higher purity, it is important to increase the purity of hemi-tartrate of compound (3). By the above crystallization, hemi-tartrate of compound (3) can be obtained with purity (e.g., purity of 98.0% or more).

Thus-obtained hemi-tartrate of compound (3) is a novel compound.

Step 2

In this step, compound (4) can be obtained by introducing a protecting group into the 1-position on the pyrrolidine of hemi-tartrate of compound (3).

The reaction depends on the kind of the protecting group at the 1-position on the pyrrolidine. For example, when the protecting group is a tert-butoxycarbonyl group, the reaction is carried out by reacting hemi-tartrate of compound (3) with a tert-butoxycarbonylation reagent in the presence of a base in a solvent.

Examples of the tert-butoxycarbonylation reagent include di-tert-butyl dicarbonate, tert-butoxycarbonyl chloride and the like.

The amount of the tert-butoxycarbonylation reagent to be used is generally 0.8 to 2.0 mol, preferably 0.9 to 1.1 mol, per 1 mol of hemi-tartrate of compound (3).

Examples of the base include organic bases. Among them, the preferred is triethylamine.

The amount of the base to be used is generally 1.5 to 3.0 mol, preferably 2.1 to 2.3 mol, per 1 mol of hemi-tartrate of compound (3).

Examples of the solvent include nitriles, ethers and the like. Among them, the preferred is acetonitrile.

The reaction is carried out generally at −5 to 35° C., preferably at 0 to 10° C. The reaction time is generally about 30 min to about 12 hr, preferably about 1 hr to about 2 hr.

After completion of the reaction, 10% aqueous citric acid solution and ethyl acetate are added to the reaction mixture, and the mixture is stirred at 20 to 30° C. for 15 min or longer, and then the aqueous layer is removed. Then, the organic layer is washed with 5% brine. The organic layer is treated with activated carbon, and then the solvent is replaced with ethanol by repeated concentration under reduced pressure and addition of ethanol. Water is added thereto at 20 to 30° C., and the mixture is cooled to 0 to 10° C., and then the seed crystals of compound (4) are added thereto to precipitate the crystals of compound (4). The mixture is stirred at 0 to 10° C. for 3 hr or longer, water is added dropwise thereto, and the mixture is stirred for 2 hr or longer. The precipitated crystals are washed with water-ethanol, and dried to give the crystals of compound (4).

The treatment method with activated carbon includes a method of adding activated carbon to the reactor, and stirred and filtered the mixture, or passing the reaction solution through a filter containing activated carbon; and then washing the insoluble substance with ethyl acetate.

Thus, compound (4) can be obtained with high purity (e.g., purity of 98% or more).

N-(4-Methylbenzene-1-sulfonyl)-L-phenylalanine salt of compound (5) obtained in Step 3b can be derived to the pharmaceutically useful N-{(2S,3S)-1-(2-hydroxy-2-methylpropanoyl)-2-[(2,3',5'-trifluoro[1,1'-biphenyl]-3-yl)methyl]pyrrolidin-3-yl}methanesulfonamide by the following Steps 4 to 7.

Step 4: a step of subjecting N-(4-methylbenzene-1-sulfonyl)-L-phenylalanine salt of compound (5) to desalting, and then the resulting compound with a methanesulfonylation reagent to give compound (6);

Step 5: a step of reacting compound (6) with (3,5-difluorophenyl) boronic acid to give compound (7);

Step 6: a step of subjecting compound (7) to a deprotection reaction to give hydrochloride of compound (8); and Step 7: a step of subjecting hydrochloride of compound (8) to a condensation reaction with 2-hydroxy-2-methylpropanoic acid to give compound (I).

Step 4

In this step, compound (6) can be obtained by subjecting N-(4-methylbenzene-1-sulfonyl)-L-phenylalanine salt of compound (5) to desalting, and then reacting the resulting compound with a methanesulfonylation reagent.

The reaction is carried out by converting N-(4-methylbenzene-1-sulfonyl)-L-phenylalanine salt of compound (5) to the free form by desalting with a base in a solvent, and then reacting the free form with a methanesulfonylation reagent in the presence of a base.

N-(4-methylbenzene-1-sulfonyl)-L-phenylalanine salt of compound (5) is preferably tert-butyl (2S,3S)-3-amino-2-[(3-bromo-2-fluorophenyl)methyl]pyrrolidine-1-carboxylate (compound (5a)) N-(4-methylbenzene-1-sulfonyl)-L-phenylalanine salt.

Examples of the base used for conversion to the free form include inorganic bases. Among them, the preferred is sodium carbonate.

Examples of the methanesulfonylation reagent include methanesulfonyl chloride and the like. The methanesulfonylation reagent may be a commercially available product.

The amount of the methanesulfonylation reagent to be used is generally 1.0 to 3.0 mol, preferably 1.3 to 1.5 mol, per 1 mol of N-(4-methylbenzene-1-sulfonyl)-L-phenylalanine salt of compound (5).

Examples of the base include organic bases. Among them, the preferred is triethylamine.

The amount of the base to be used is generally 1.5 to 4.0 mol, preferably 1.9 to 2.1 mol, per 1 mol of N-(4-methylbenzene-1-sulfonyl)-L-phenylalanine salt of compound (5).

Examples of the solvent include esters; aromatic hydrocarbons; amides and the like. Among them, the preferred is a mixed solvent of ethyl acetate and toluene.

The reaction is carried out generally at −10 to 15° C., preferably at −2 to 8° C. The reaction time is generally about 30 min to about 6 hr, preferably about 1 hr to about 2 hr.

After completion of the reaction, conventional workup such as phase separation, concentration and the like is performed. Then, compound (6) is precipitated by addition of a saturated hydrocarbon such as n-heptane and the like. If necessary, compound (6) may be recrystallized from an aromatic hydrocarbon such as toluene and the like and a saturated hydrocarbon such as n-heptane and the like.

Thus, the crystals of compound (6) can be obtained.

Step 5

In this step, compound (7) can be obtained by reacting compound (6) with (3,5-difluorophenyl) boronic acid.

The reaction is carried out by reacting compound (6) with (3,5-difluorophenyl) boronic acid in the presence of a palladium catalyst, a phosphine ligand and a base, in a solvent.

Compound (6) is preferably tert-butyl (2S,3S)-2-[(3-bromo-2-fluorophenyl)methyl]-3-[(methanesulfonyl) amino]pyrrolidine-1-carboxylate (compound (6a)).

(3,5-Difluorophenyl) boronic acid may be a commercially available product.

The amount of (3,5-difluorophenyl) boronic acid to be used is generally 1.0 to 3.0 mol, preferably 1.1 to 1.3 mol, per 1 mol of compound (6).

Examples of the palladium catalyst include Pd carbon powder, di-tert-butyl (3-methyl-2-butenyl)phosphine (Pd (m-Crophos)$Cl_2$), palladium (II) acetate, tetrakis(triphenylphosphine)palladium (0), dichlorobis(triphenylphosphine)palladium (II), dichlorobis(triethylphosphine)palladium (II), tris (dibenzylideneacetone)dipalladium (0), 1,1'-bis(diphenylphosphino)ferrocenepalladium (II) chloride and the like. The palladium catalyst is preferably di-tert-butyl (3-methyl-2-butenyl)phosphine (Pd(m-Crophos)$Cl_2$) or Pd carbon powder, particularly preferably 10% Pd carbon powder (e.g. PE-TYPE, manufactured by N. E. CHEMCAT).

The amount of the palladium catalyst to be used is catalytic amount, specifically, generally 0.01 to 2.00 mol %, preferably 0.08 to 0.12 mol %, per 1 mol of compound (6).

Examples of the phosphine ligand include Xphos (2-dicyclohexylphosphino-2',4',6'-triisopropylbiphenyl), Xantphos (4,5-bis(diphenylphosphino)-9,9-dimethylxanthene) and the like. The phosphine ligand is preferably Xphos (2-dicyclohexylphosphino-2',4',6'-triisopropylbiphenyl).

The amount of the phosphine ligand to be used is catalytic amount, specifically, generally 0.02 to 4.00 mol %, preferably 0.16 to 0.24 mol %, per 1 mol of compound (6).

Examples of the base include organic bases and inorganic bases. The base is preferably N,N-diisopropylethylamine or sodium hydroxide, particularly preferably sodium hydroxide.

The amount of the base to be used is generally 1.0 to 3.0 mol, preferably 1.4 to 1.6 mol, per 1 mol of compound (6).

The solvent is preferably ethers, or a mixture of ether and water, and more preferably a mixture of water and 1,2-dimethoxyethane.

The reaction is carried out generally at 70 to 83° C., preferably at 75 to 81° C. The reaction time is generally about 1 hr to about 12 hr, preferably about 3 hr to about 6 hr.

After completion of the reaction, ethyl acetate and water are added to the reaction mixture, and then, the insoluble substance is removed by filtration. The filtrate is treated with N-acetyl cysteine and NaCl, and the solvent is replaced with ethanol by concentration. Water is added thereto at 60 to 70° C., and the mixture is cooled to 20 to 30° C. to precipitate the crystals of compound (7). The precipitated crystals are washed with ethanol-water, and dried. Thus, the crystals of compound (7) can be obtained.

Step 6

In this step, hydrochloride of compound (8) can be obtained by subjecting compound (7) to a deprotection reaction.

Compound (7) is preferably tert-butyl (2S,3S)-3-[(methanesulfonyl)amino]-2-[(2,3',5'-trifluoro[1,1'-biphenyl]-3-yl) methyl]pyrrolidine-1-carboxylate (compound (7a)). In this case, the reaction is carried out by reacting compound (7) with an acid in a solvent.

Examples of the acid include hydrogen chloride and the like. Hydrogen chloride is used preferably as a solution in an organic solvent, more preferably as a solution of hydrogen chloride in 2-propanol or ethyl acetate, particularly preferably as a solution of hydrogen chloride in 2-propanol.

Examples of the solvent include alcohols, esters, water and the like. The solvent is preferably alcohols, esters or mixed solvents thereof, more preferably ethanol, ethyl acetate, 2-propanol or mixed solvents thereof, particularly preferably 2-propanol.

The reaction is carried out generally at 40 to 80° C., preferably at 50 to 70° C. The reaction time is generally about 1 hr to about 12 hr, preferably about 2 hr to about 8 hr.

After completion of the reaction, n-heptane is added to the reaction mixture at 40 to 80° C. to precipitate crystals, the mixture is cooled to 0 to 10° C. over 1 hr or longer, and the crystals are washed with 2-propanol/n-heptane or ethanol/n-heptane, preferably 2-propanol/n-heptane. Thus, the crystals of hydrochloride of compound (8) can be obtained.

Step 7

In this step, compound (I) can be obtained by subjecting hydrochloride of compound (8) to a condensation reaction with 2-hydroxy-2-methylpropanoic acid.

The condensation reaction is carried out by reacting hydrochloride of compound (8) with 2-hydroxy-2-methylpropanoic acid in the presence of a condensation reagents and a base.

2-Hydroxy-2-methylpropanoic acid may be a commercially available product.

The amount of 2-hydroxy-2-methylpropanoic acid to be used is generally 1.5 to 5.0 mol, preferably 2.4 to 2.6 mol, per 1 mol of hydrochloride of compound (8).

Examples of the base include organic bases and inorganic bases. The base is preferably triethylamine.

The amount of the base to be used is generally 1.5 to 7.5 mol, preferably 3.6 to 3.8 mol, per 1 mol of hydrochloride of compound (8).

Examples of the condensation reagents include carbodiimide condensation reagents such as 1-ethyl-3-(3-dimethylaminopropyl) carbodiimide hydrochloride (WSCD) and the like; triazine condensation reagents such as 4-(4,6- dimethoxy-1,3,5-triazin-2-yl)-4-methylmorpholinium chloride-n-hydrate (DMT-MM) and the like; carbonate ester condensation reagents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as chloroethyl formate and the like; O-(7-azabenzotriazol-1-yl)-N,N, N',N'-tetramethyluronium hexafluorophosphorate (HATU); sulfuric acid; combinations thereof and the like. When carbodiimide condensation reagents is used, an additive such as 1-hydroxybenzotriazole (HOBt) monohydrate, N-hydroxysuccinimide (HOSu), N-hydroxy-5-norbornene-2,3-dicarboxyimide (HONB), dimethylaminopyridine (DMAP) and the like may be added to the reaction system. The condensation reagents is preferably CDI or WSCD. The condensation reagents is particularly preferably CDI. The additive is preferably HOBt monohydrate or HONB. The additive is particularly preferably HONB.

The amount of the condensation reagents to be used is generally 1.5 to 5.0 mol, preferably 2.4 to 2.6 mol, per 1 mol of hydrochloride of compound (8).

The amount of the additive to be used is generally 1.5 to 5.0 mol, preferably 2.2 to 2.4 mol, per 1 mol of hydrochloride of compound (8).

The reaction is carried out generally in a solvent. Examples of the solvent include amides and the like. The solvent is preferably amides, more preferably dimethylacetamide.

The reaction is carried out generally at 20 to 50° C., preferably at 32 to 42° C. The reaction time is generally about 2 hr to about 24 hr, preferably about 4 hr to about 8 hr.

After completion of the reaction, water is added to the reaction mixture, the pH is adjusted to alkaline with sodium hydroxide, and the mixture is stirred under heating. Then, the pH is adjusted to neutral with hydrochloric acid at room temperature, and water is added thereto to precipitate the crystals of compound (I). If necessary, the seed crystals (e.g., the seed crystals of the sesqui-hydrate) may be added thereto. For example, water is added to the mixture at 15 to 45° C., the pH is adjusted to 13.0 to 14.0 with sodium hydroxide, and the mixture is stirred at 40 to 60° C. Then, the mixture is cooled to 20 to 40° C., and the pH is adjusted to 7.5 to 8.5 with hydrochloric acid. Then, water is added dropwise thereto at 55 to 65° C., the seed crystals are added thereto, and the mixture is stirred at 55 to 65° C. Then, water is added dropwise thereto at 55 to 65° C., and the mixture is cooled to 45 to 55° C. over 0.5 hr or longer, and then cooled to 30° C. or lower over 1.5 hr or longer to precipitate the crystals of compound (I). The precipitated crystals are washed with ethanol-water to give the crystals of compound (I). If necessary, the crystals may be agitated in ethanol-water-triethylamine, or recrystallized from ethanol-water. If necessary, the solution of compound (I) may be passed through a filter with activated carbon before recrystallization by ethanol-water.

Thus, the crystals of compound (I) can be obtained with high purity (e.g., purity of 99% or more)

Compound (I) may be a hydrate, a non-hydrate or a solvate. Compound (I) is preferably a hydrate (preferably a sesqui-hydrate).

EXAMPLES

The present invention is explained in detail in the following by referring to Examples. However, the examples do not limit the present invention and the examples can be modified within the scope of the present invention.

The "room temperature" in the following Examples is generally about 10° C. to about 35° C. The ratio for mixed solvent is unless otherwise specified, a volume mixing ratio, and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as elution solvent in column chromatography was used as eluent, and UV detector was used for the detection. In silica gel column chromatography, the indication of NH means use of aminopropylsilane-bonded silica gel and the indication of DIOL means use of 3-(2,3-dihydroxypropoxy) propylsilane-bonded silica gel. In preparative HPLC (high-performance liquid chromatography), the indication of C18 means use of octadecyl-bonded silica gel. The ratio for elution solvent is unless otherwise specified, a volume mixing ratio. The temperatures in the reaction and treatment operations described in Reference Examples and Examples include variations in the range of ±5° C.

$^1$H NMR was measured by Fourier transform NMR. For the analysis of $^1$H NMR, ACD/SpecManager (trade name) software and the like were used. Peaks of a hydroxyl group, an amino group and the like, having broad proton peak, are not sometimes described.

In the following Examples, the following abbreviations are used.

M: molar concentration

N: normality

HPLC: high-performance liquid chromatography

Experimental Example 1

Screening of Chiral Ligand

Chiral ligands were screened in order to identify the most suitable metal complexes for the asymmetric reductive amination reaction of the present invention.

$[RuCl_2(benzene)]_2$ (0.0010 g), a chiral ligand, and ammonium salicylate or ammonium acetate (5.0 equivalent) were charged to a reactor. Then, a solution of tert-butyl 2-[(3-bromo-2-fluorophenyl)methyl]-3-oxopyrrolidine-1-carboxylate (compound (4a)) (0.7445 g)/methanol (25 ml) was prepared, and 1 ml of the solution was added thereto. The mixture was stirred at 50° C. for about 1 hr under nitrogen atmosphere, and then stirred under hydrogen pressure of 5.0 MPa (G) at 80° C. for 16 hr to give a mixture containing the desired compound tert-butyl (2S,3S)-3-amino-2-[(3-bromo-2-fluorophenyl)methyl]pyrrolidine-1-carboxylate (compound (5a)).

The obtained mixture containing compound (5a) was subjected to chiral HPLC analysis under the following conditions, and the yield (HPLC amine area %) of the cis-form, the amine selectivity and the enantiomeric excess (% ee of cis) were calculated. The results are shown in Table 4.

The abbreviations are as follows.

(2S,3S)-form: tert-butyl (2,3S)-3-amino-2-[(3-bromo-2-fluorophenyl)methyl]pyrrolidine-1-carboxylate (compound (5a))

(2R,3R)-form: tert-butyl (2R,3R)-3-amino-2-[(3-bromo-2-fluorophenyl)methyl]pyrrolidine-1-carboxylate trans-form: tert-butyl trans-3-amino-2-[(3-bromo-2-fluorophenyl)methyl]pyrrolidine-1-carboxylate (HPLC Analysis Condition)

Yield of Cis-Form (HPLC Amine Area %) and Amine Selectivity column: YMC-Pack C18 Pro RS, 5 μm, 4.6×150 mm
mobile phase: A solution) $CH_3CN$
B solution) 0.03M $K_2HPO_4$
flow rate: 1.0 mL/min
column temperature: 25° C.
detection: UV 220 nm
injection: 10 mL
analysis time: 30 min
gradient program:

TABLE 1

| Time (min) | Mobile Phase A(%) | Mobile Phase B(%) |
|---|---|---|
| 0.00 | 90 | 10 |
| 2.00 | 90 | 10 |
| 15.00 | 30 | 70 |
| 30.00 | 30 | 70 |
| 33.00 | 90 | 10 |
| 40.00 | 90 | 10 |

retention time:
(2S,3S)-form 15.02 min
trans-form 15.78 min

Enantiomeric Excess (% ee of cis)

$$\%\ ee \text{ of } cis = \{[HPLC \text{ area of } (2R, 3R)-\text{form} - HPLC \text{ area of } (2S, 3S)-\text{form}] / [HPLC \text{ area of } (2R, 3R)-\text{form} + HPLC \text{ area of } (2S, 3S)-\text{form}]\} \times 100$$

In the Case of (R,R)-iPr-DUPHOS or (R)-PHANEPHOS column: Chiralpak (Daicel), 5 μm, 4.6×150 mm
mobile phase: A solution) 0.01M $K_2HPO_4$
B solution) $CH_3CN$
flow rate: 1.0 mL/min
column temperature: 25° C.
detection: UV 220 nm
injection: 10 μL
analysis time: 20 min
gradient program:

TABLE 2

| Time (min) | Mobile Phase A(%) | Mobile Phase B(%) |
|---|---|---|
| 0:00 | 55 | 45 |
| 7:00 | 55 | 45 |
| 10:00 | 20 | 80 |
| 20:00 | 20 | 80 |
| 22:00 | 55 | 45 |
| 30:00 | 55 | 45 |

retention time:
(2S,3S)-form 6.48 min
(2R,3R)-form 15.77 min

In the Case of Other than (R,R)-iPr-DUPHOS and (R)-PHANEPHOS column: Chiralpak IE (Daicel), 5 μm, 4.6×250 mm
mobile phase: A solution) 0.01M $K_2HPO_4$
B solution) $CH_3CN$
flow rate: 1.0 mL/min
column temperature: 25° C.
detection: UV 220 nm
injection: 10 μL
analysis time: 30 min
gradient program:

TABLE 3

| Time (min) | Mobile Phase A(%) | Mobile Phase B(%) |
|---|---|---|
| 0:00 | 45 | 55 |
| 10:00 | 45 | 55 |
| 15:00 | 30 | 70 |
| 23:00 | 30 | 70 |
| 23:01 | 45 | 55 |
| 30:00 | 45 | 55 |

retention time:
tert-butyl 2-[(3-bromo-2-fluorophenyl)methyl]-3-hydroxypyrrolidine-1-carboxylate (stereoisomer mixture) 6.90 min
(2S,3S)-form 8.84 min
(2R,3R)-form 9.95 min
compound (4a) 11.02 min

TABLE 4

| Ligand | HPLC amine area % | Amine selectivity | % ee of cis | ligand amount (g) |
|---|---|---|---|---|
| (S)-BINAP | 78.4 | 93.4 | −25.3 | 0.0027 |
| (R)-Xylyl-BINAP | 78.5 | 94.1 | 45.0 | 0.0032 |
| (R)-Xylyl-BINAP | 89.1 | 94.2 | 43.9 | 0.0032 |
| (R,R)-iPr-DUPHOS | 84.1 | 92.8 | −20.4 | 0.0018 |
| (R)-PHANEPHOS | 81.2 | 94.2 | 25.1 | 0.0025 |
| (R) (S)-SL-J003 | 81.9 | 91.7 | 39.1 | 0.0027 |
| (R) (R)-SL-T001 | 47.5 | 82.8 | 43.4 | 0.003 |
| (R)-p-tol-BINAP | 89.6 | 93.3 | 30.6 | 0.003 |
| (S)-m-tol-BINAP | 80.0 | 95.1 | −38.8 | 0.003 |
| (S)-DMANYL-BINAP | 74.5 | 93.3 | −44.0 | 0.0038 |
| (S)-DADMP-BINAP | 66.8 | 87.2 | −41.7 | 0.004 |
| (R)-H8-BINAP | 83.6 | 95.6 | 40.1 | 0.0028 |
| (R)-SYNPHOS | 61.7 | 95.2 | 30.4 | 0.0028 |
| (R)-SOLPHOS | 73.8 | 95.4 | −36.1 | 0.0029 |
| (R)-Xylyl-PHANEPHOS | 83.7 | 93.4 | −70.5 | 0.003 |
| (R)(R)-SL-W002 | 56.4 | 79.8 | 22.2 | 0.0029 |
| (S)-PMP-BINAP | 63.9 | 95.5 | −32.9 | 0.0033 |
| (S)-BOP-BINAP | 44.3 | 93.0 | −36.4 | 0.0035 |
| (R)-MeO-BIPHEP | 61.5 | 95.5 | 28.9 | 0.0026 |
| (R)-ClMeO-BIPHEP | 75.8 | 93.9 | 28.3 | 0.0029 |

From Table 4, it was shown that among these, the BINAP, phosphine, ferrocene and cyclophane chiral ligands have good reaction efficiency and high enantioselectivity.

Experimental Example 2-1

Screening of Metal Catalyst

Metal catalysts were screened in order to identify the most suitable metal complexes for the asymmetric reductive amination reaction of the present invention.

A metal catalyst (0.0010 g) and a chiral ligand (1.1 equivalent) were charged to a reactor. Then a solution of tert-butyl 2-[(3-bromo-2-fluorophenyl)methyl]-3-oxopyrrolidine-1-carboxylate (compound (4a)) (0.2978 g)/methanol (5 ml) was prepared, and 0.5 ml of the solution was added thereto. Then, a solution of $NH_4OAc$ (0.0308 g)/methanol (5 ml) was prepared, 0.5 ml of the solution was added thereto, and the mixture was stirred for 30 min. The mixture was stirred under hydrogen pressure of 5.0 MPa (G) at 80° C. for 17 hr to give a mixture containing the desired compound tert-butyl (2S,3S)-3-amino-2-[(3-bromo-2-fluorophenyl)methyl]pyrrolidine-1-carboxylate (compound (5a)).

The obtained mixture containing compound (5a) was subjected to chiral HPLC analysis under following conditions, and the yield (HPLC amine area %) of the cis-form and the enantiomeric excess (% ee of cis) were calculated. The results are shown in Table 7.

The abbreviations are as follows.

(2,3S)-form: tert-butyl (2S,3S)-3-amino-2-[(3-bromo-2-fluorophenyl)methyl]pyrrolidine-1-carboxylate (=compound (5a))

(2R,3R)-form: tert-butyl (2R,3R)-3-amino-2-[(3-bromo-2-fluorophenyl)methyl]pyrrolidine-1-carboxylate trans-form: tert-butyl trans-3-amino-2-[(3-bromo-2-fluorophenyl)methyl]pyrrolidine-1-carboxylate (HPLC Analysis Condition)

Yield (HPLC Amine Area %) of cis-Form column: YMC-Pack C18 Pro RS, 5 μm, 4.6×150 mm mobile phase: A solution) 0.03M $K_2HPO_4$ B solution) $CH_3CN$ flow rate: 1.0 mL/min column temperature: 25° C.

detection: UV 220 nm injection: 10 mL analysis time: 30 min gradient program:

TABLE 5

| Time (min) | Mobile Phase A(%) | Mobile Phase B(%) |
|---|---|---|
| 0.00 | 90 | 10 |
| 2.00 | 90 | 10 |
| 15.00 | 30 | 70 |
| 30.00 | 30 | 70 |
| 33.00 | 90 | 10 |
| 40.00 | 90 | 10 |

retention time:

(2S,3S)-form 15.02 min trans-form 15.78 min

Enantiomeric Excess (% ee of cis)

$$\%\ ee \text{ of } cis = \{[HPLC \text{ area of } (2R, 3R)-\text{form} - HPLC \text{ area of } (2S, 3S)-\text{form}]/[HPLC \text{ area of } (2R, 3R)-\text{form} + HPLC \text{ area of } (2S, 3S)-\text{form}]\}\times 100$$

column: Chiralpak IE (Daicel), 5 μm, 4.6×250 mm mobile phase: A solution) 0.01M $K_2HPO_4$ B solution) $CH_3CN$ flow rate: 1.0 mL/min column temperature: 25° C.

detection: UV 220 nm injection: 10 μL analysis time: 30 min gradient program:

TABLE 6

| Time (min) | Mobile Phase A (%) | Mobile Phase B (%) |
|---|---|---|
| 0:00 | 45 | 55 |
| 10:00 | 45 | 55 |
| 15:00 | 30 | 70 |
| 23:00 | 30 | 70 |
| 23:01 | 45 | 55 |
| 30:00 | 45 | 55 |

retention time:

tert-butyl 2-[(3-bromo-2-fluorophenyl)methyl]-3-hydroxypyrrolidine-1-carboxylate (stereoisomer mixture) 6.90 min (2S,3S)-form 8.84 min (2R,3R)-form 9.95 min compound (4a) 11.02 min

TABLE 7

| Catalyst | Ligand | HPLC amine area % | % ee of cis |
|---|---|---|---|
| $[RhCl(cod)]_2$ | (S)-BINAP | 31.3 | −2.0 |
| $[RhCl(cod)]_2$ | (R)-Xylyl-BINAP | 61.1 | 5.0 |
| $[RhCl(cod)]_2$ | (R, R)-Skewphos | 23.4 | 5.4 |
| $[RhCl(cod)]_2$ | (R, R)-PTBP-Skewphos | 51.1 | 7.2 |
| $[RhCl(cod)]_2$ | (R) (S)-JOSIPHOS | 33.4 | 22.7 |
| $[RhCl(cod)]_2$ | (R, R)-iPr-DUPHOS | 37.4 | 17.1 |
| $[RhCl(cod)]_2$ | (R)-PHANEPHOS | 25.6 | 21.8 |
| $[RhCl(cod)]_2$ | (R)-MONOPHOS | 53.0 | −2.3 |
| $[Rh(cod)_2]$ OTf | (S)-BINAP | 13.1 | 4.7 |
| $[Rh(cod)_2]$ OTf | (R)-Xylyl-BINAP | 55.6 | 15.2 |
| $[Rh(cod)_2]$ OTf | (R, R)-Skewphos | 31.8 | −13.2 |
| $[Rh(cod)_2]$ OTf | (R, R)-PTBP-Skewphos | 23.0 | −14.3 |
| $[Rh(cod)_2]$ OTf | (R) (S)-JOSIPHOS | 27.7 | −33.8 |
| $[Rh(cod)_2]$ OTf | (R, R)-iPr-DUPHOS | 29.1 | −4.8 |
| $[Rh(cod)_2]$ OTf | (R)-PHANEPHOS | 24.3 | 1.2 |
| $[Rh(cod)_2]$ OTf | (R)-MONOPHOS | 18.1 | 10.2 |
| $[IrCl(cod)]_2$ | (S)-BINAP | 13.3 | 6.7 |
| $[IrCl(cod)]_2$ | (R)-Xylyl-BINAP | 50.3 | 13.4 |
| $[IrCl(cod)]_2$ | (R, R)-Skewphos | 33.6 | −9.8 |
| $[IrCl(cod)]_2$ | (R, R)-PTBP-Skewphos | 23.6 | −11.8 |
| $[IrCl(cod)]_2$ | (R) (S)-JOSIPHOS | 28.1 | −37.5 |
| $[IrCl(cod)]_2$ | (R, R)-iPr-DUPHOS | 35.1 | −2.1 |
| $[IrCl(cod)]_2$ | (R)-PHANEPHOS | 21.7 | 2.3 |
| $[IrCl(cod)]_2$ | (R)-MONOPHOS | 20.6 | 13.8 |
| $[Ir(cod)_2]$ BARF | (S)-BINAP | 33.4 | −2.2 |
| $[Ir(cod)_2]$ BARF | (R)-Xylyl-BINAP | 25.2 | 8.7 |
| $[Ir(cod)_2]$ BARF | (R, R)-Skewphos | 34.2 | 13.7 |
| $[Ir(cod)_2]$ BARF | (R, R)-PTBP-Skewphos | 29.3 | 12.6 |
| $[Ir(cod)_2]$ BARF | (R) (S)-JOSIPHOS | 39.6 | 5.3 |
| $[Ir(cod)_2]$ BARF | (R, R)-iPr-DUPHOS | 25.5 | 4.0 |
| $[Ir(cod)_2]$ BARF | (R)-PHANEPHOS | 50.3 | 6.6 |

From Table 7, it was shown that the rhodium and iridium metal catalysts have good reaction efficiency and high enantioselectivity in combination with various chiral ligands.

Experimental Example 2-2

Screening of Metal Catalyst

Ruthenium metal catalysts were screened in order to identify the most suitable metal complexes for the asymmetric reductive amination reaction of the present invention.

[RuCl(p-cymene) ((R)-xylyl-binap)]Cl and $RuCl_2$((R)-xylyl-binap) (dmf)n

A ruthenium complex was charged to a reactor, and then a solution of tert-butyl 2-[(3-bromo-2-fluorophenyl)methyl]-3-oxopyrrolidine-1-carboxylate (compound (4a), 1.1911 g)/methanol (10 ml) was prepared, and 0.5 ml of the solution was added to the reactor. Then, a solution of $NH_4OAc$ (1.2333 g)/methanol (10 ml) was prepared, and 0.5 ml of the solution was added to the reactor. The mixture was stirred, and then stirred under hydrogen pressure of 5.0 MPa (G) at 80° C. for about 18 hr to give a mixture containing tert-butyl (2S,3S)-3-amino-2-(3-bromo-2-fluorobenzyl) pyrrolidine-1-carboxylate (compound (5a)).

$(NH_2Me_2)$ $[(RuCl((R)\text{-xylyl-binap}))_2(\eta\text{-}Cl)_3]$, $Ru(TFA)_2$((R)-xylyl-binap) and $Ru(OAc)_2$((R)-xylyl-binap)

A ruthenium complex was charged to a reactor. Then, a solution of compound (4a) (0.5956 g)/methanol (5 ml) was prepared, and 0.5 ml of the solution was added thereto. Then, a solution of $NH_4OAc$ (0.6166 g)/methanol (5 ml) was prepared, and 0.5 ml of the solution was added thereto. The mixture was stirred, and then stirred under hydrogen pressure of 5.0 MPa (G) at 80° C. to give a mixture containing compound (5a).

The obtained mixture containing compound (5a) was subjected to HPLC analysis under following conditions, and the conversion rate of the reaction, the formation ratio of cis-form/trans-form (cis/trans) and the enantiomeric excess (% ee of cis) were calculated. The results are shown in Table 10.

The abbreviations are as follows.

(2S,3S)-form: tert-butyl (2,3S)-3-amino-2-[(3-bromo-2-fluorophenyl)methyl]pyrrolidine-1-carboxylate (compound (5a))

(2R,3R)-form: tert-butyl (2R,3R)-3-amino-2-[(3-bromo-2-fluorophenyl)methyl]pyrrolidine-1-carboxylate trans-form: tert-butyl trans-3-amino-2-[(3-bromo-2-fluorophenyl)methyl]pyrrolidine-1-carboxylate (HPLC Analysis Condition)

Conversion Rate and Formation Ratio of cis-form/trans-form (cis/trans)

$$cis/trans = (HPLC \text{ area of } cis\text{-form})/[HPLC \text{ area of } cis\text{-form}) + (HPLC \text{ area of } trans\text{-form})] \times 100$$

column: YMC-Pack C18 Pro RS, 5 μm, 4.6×150 mm
mobile phase: A solution) 0.03M $K_2HPO_4$
B solution) $CH_3CN$
flow rate: 1.0 mL/min
column temperature: 25° C.
detection: UV 220 nm
injection: 10 mL
analysis time: 30 min
gradient program:

TABLE 8

| Time (min) | Mobile Phase A (%) | Mobile Phase B (%) |
|---|---|---|
| 0.00 | 90 | 10 |
| 2.00 | 90 | 10 |
| 15.00 | 30 | 70 |
| 30.00 | 30 | 70 |
| 33.00 | 90 | 10 |
| 40.00 | 90 | 10 |

retention time:
(2S,3S)-form 15.02 min
trans-form 15.78 min

Enantiomeric Excess (% ee of cis)

$$\% \ ee \text{ of } cis = \{[HPLC \text{ area of } (2R, 3R)-\text{form} - HPLC \text{ area of } (2S, 3S)-\text{form}]/[HPLC \text{ area of } (2R, 3R)-\text{form} + HPLC \text{ area of } (2S, 3S)-\text{form}]\} \times 100$$

column: Chiralpak IE (Daicel), 5 μm, 4.6×250 mm
mobile phase: A solution) 0.01M $K_2HPO_4$
B solution) $CH_3CN$
flow rate: 1.0 mL/min
column temperature: 25° C.
detection: UV 220 nm
injection: 10 μL
analysis time: 30 min
gradient program:

TABLE 9

| Time (min) | Mobile Phase A (%) | Mobile Phase B (%) |
|---|---|---|
| 0:00 | 45 | 55 |
| 10:00 | 45 | 55 |
| 15:00 | 30 | 70 |
| 23:00 | 30 | 70 |
| 23:01 | 45 | 55 |
| 30:00 | 45 | 55 |

retention time:
tert-butyl (2S,3S)-2-[(3-bromo-2-fluorophenyl)methyl]-3-hydroxypyrrolidine-1-carboxylate 6.90 min
(2S,3S)-form 8.44 min
(2R,3R)-form 9.55 min
compound (4a) 10.89 min
trans-form 11.02 min

TABLE 10

| Catalyst | Conversion rate | cis/trans | % ee of cis | catalyst amount (g) |
|---|---|---|---|---|
| [RuCl (p-cymene) ((R)-xylyl-binap)] Cl | 100.00 | 95.0 | 63.1 | 0.0033 |
| $RuCl_2$ ((R)-xylyl-binap) (dmf) n | 100.00 | 94.8 | 60.2 | 0.0034 |
| $(NH_2Me_2)$ [(RuCl ((R)-xylyl-binap))$_2$ (η-Cl)$_3$] | 100.00 | 94.1 | 59.1 | 0.0030 |
| Ru $(TFA)_2$ ((R)-xylyl-binap) | 100.00 | 94.4 | 63.8 | 0.0034 |
| Ru $(OAc)_2$ ((R)-xylyl-binap) | 100.00 | 94.2 | 65.2 | 0.0031 |

From Table 10, it was shown that the various ruthenium metals have good reaction efficiency and high enantioselectivity.

Example 1

Synthesis of 2-[(3-bromo-2-fluorophenyl)methyl]pyrrolidin-3-one hemi-tartrate (hemi-tartrate of Compound (3))

tert-Butyl 3-oxopyrrolidine-1-carboxylate (compound (2a), 6.91 g) and toluene (45 ml) were charged to a reactor, and then pyrrolidine (3.32 g) was added dropwise thereto at 40° C. or lower, and the mixture was stirred for 10 min. The reaction solution was concentrated to 25 ml, to the concentrated solution was added toluene (25 ml), and the solution was concentrated to 25 ml. Again, to the concentrated solution was added toluene (25 ml), and the solution was concentrated to 25 ml. To the obtained concentrated solution was added acetonitrile (40 ml), and then tetrabutylammonium iodide (0.689 g) was added thereto. The temperature of the mixture was maintained at about 30° C., and an acetonitrile solution (7.5 ml) of 1-bromo-3-(bromomethyl)-2-fluorobenzene (compound (1), 5.00 g) was added dropwise thereto. The dropping funnel used was washed with acetonitrile (2.5 ml), the washing was added thereto, and the mixture was stirred at 40° C. for 1 hr. Then, the mixture was cooled to 15 to 25° C., and the pH was adjusted to 2.0 to 3.0 with 2M hydrochloric acid. Ethyl acetate (40 ml) was added thereto, and the mixture was allowed to stand, and the aqueous layer was removed by separation to give an organic layer. To the obtained organic layer was added 10% aqueous sodium thiosulfate solution (35 ml), and the mixture was allowed to stand, and the aqueous layer was removed by separation to give an organic layer. To the obtained organic layer was added 10% brine (35 ml), and the mixture was allowed to stand. The aqueous layer was removed by separation, and the obtained organic layer was concentrated to 15 ml.

To the concentrated solution was added 2-propanol (40 ml), and the mixture was concentrated to 15 ml. Again, to the concentrated solution was added 2-propanol (40 ml), and the mixture was concentrated to 15 ml. The concentrated solution was heated to 50° C., and while maintaining the temperature, 5M hydrogen chloride/2-propanol (15 ml) was added dropwise thereto to precipitate crystals. The solution in which crystallization occurred was stirred at 50° C. for 1 hr. Ethyl acetate (50 ml) was slowly added thereto at 50° C., and the mixture was stirred at 50° C. for 1 hr. The mixture was slowly cooled to 5° C., and stirred at 5° C. for 1 hr, and the crystals were collected by filtration, and washed with ethyl acetate (15 ml). Thus-obtained wet crystals of the hydrochloride of compound (3) and toluene (40 ml) were placed into a reactor, and the mixture was cooled to 5° C. Triethylamine (2.27 g) was added dropwise thereto at 5° C. The mixture was stirred at 5° C. for 1 hr, and the insoluble substance was removed by filtration, and washed with toluene (25 ml), and the washing was combined with the filtrate.

Methanol (50 ml) and DL-tartaric acid (1.40 g) were charged to another reactor, and the mixture was stirred at 25° C. for 30 min. The above filtrate was added dropwise thereto at 25° C. over 2 hr or longer to precipitate crystals. The dropping funnel used was washed with toluene (5 ml), and the washing was combined with the above mixture. The mixture was stirred at 25° C. for 1 hr, slowly cooled to 5° C. with stirring, and stirred at 5° C. for 3 hr or longer. The precipitated crystals were collected by filtration, washed with toluene-methanol=2:1 (15 ml) solution cooled to 5° C., and dried under reduced pressure to give crystals (3.35 g) (98.0 HPLC area %) of the titled hemi-tartrate of compound (3).

(Compound NMR Data)

$^{1}$H NMR (300 MHz, DMSO-$d_6$) δ=7.56 (t, J=7.3 Hz, 1H), 7.34 (t, J=7.3 Hz, 1H), 7.10 (t, J=7.3 Hz, 1H), 4.16 (m, 1H), 3.38 (dd, J=4.3, 9.3 Hz, 1H), 3.22 (m, 1H), 3.12-2.99 (m, 2H), 2.70 (dd, J=9.3, 14.2 Hz, 1H), 2.47-2.17 (m, 2H)

(HPLC Analysis Condition)

column: YMC-Pack Pro C18 (YMC. Co., Ltd.), column size 4.6×150 mm, particle size 5 μm column temperature: 40° C.

mobile phase: A solution) 0.02M $K_2HPO_4$ (pH7.0): $CH_3CN$=70:30

B solution) 0.02M $K_2HPO_4$ (pH7.0): $CH_3CN$=30:70 gradient program:

TABLE 11

| Time (min) | Mobile Phase A (%) | Mobile Phase B (%) |
|---|---|---|
| 0:00 | 100 | 0 |
| 15:00 | 0 | 100 |
| 35:00 | 0 | 100 |
| 35:01 | 100 | 0 |
| 40:01 | 100 | 0 |

flow rate: 1.0 ml/min retention time:

compound (1) 15.7 min tert-butyl 2-[(3-bromo-2-fluorophenyl)methyl]-3-oxopyrrolidine-1-carboxylate (compound (4a)) 16.5 min compound (3) 7.7 min DL-tartaric acid 1.4 min

Example 2

Synthesis of tert-butyl 2-[(3-bromo-2-fluorophenyl) methyl]-3-oxopyrrolidine-1-carboxylate (Compound (4a))

Hemi-tartrate of compound (3) (10.0 g) and acetonitrile (60 ml) were charged to a reactor, and triethylamine (6.4 g) was added dropwise thereto while maintaining the temperature at 25° C. $Boc_2O$ (6.3 g) and acetonitrile (15 ml) were charged to another reactor, and the mixture was stirred at 25° C., and added dropwise to a solution of the above compound (3), and the dropping funnel used was washed with acetonitrile (5 ml), and the washing was added to the reactor. Thus-obtained mixture was stirred at 25° C. for 1 hr. 10% Aqueous citric acid solution (50 ml) and ethyl acetate (80 ml) were added thereto, and the mixture was allowed to stand at 25° C., and the aqueous layer was removed by separation. To the obtained organic layer was added 5% brine (50 ml), and the mixture was allowed to stand at 25° C., and the aqueous layer was removed by separation to give an organic layer. To the obtained organic layer was added activated carbon SHIRASAGI A (Osaka Gas Chemicals) (1.0 g), and the mixture was stirred at 25° C. for 30 min or longer. The insoluble substance was removed by filtration, and washed with ethyl acetate (30 ml), and the washing was combined with the filtrate. The filtrate was concentrated at 40° C. or lower to the volume of 30 ml. Ethanol (100 ml) was added thereto, and the mixture was concentrated to 30 ml at 40° C. or lower. Ethanol (100 ml) was added again to the concentrated solution, and the mixture was concentrated to 30 ml at 40° C. or lower. Ethanol (20 ml) was added to the concentrated solution at 25° C., and water (20 ml) was added dropwise thereto at 25° C. The mixture was cooled to 5° C., the seed crystals (5 mg) of compound (4a) were added thereto at 5° C., and after confirmation of the crystallization, the mixture was stirred at 5° C. for 6 hr or longer. Water (50 ml) was added dropwise thereto, and the mixture was stirred at 5° C. for 1 hr or longer. After stirring at 5° C. for additional 2 hr, and the crystals were collected by filtration, and washed with ethanol-water=1:2 (30 ml) cooled to 3° C. The drained wet crystals were dried under reduced pressure at 25° C. or lower to give wet crystals (10.73 g) (99.5 HPLC area %) of the titled compound (4a). As the seed crystals of compound (4a), the crystals spontaneously precipitate prior to the addition of the seed crystals in the reaction described above were used.

(Compound NMR Data)

$^{1}$H NMR (300 MHz, DMSO-$d_6$) δ=7.58 (t, J=7.0 Hz, 1H), 7.20-7.04 (m, 2H), 4.12 (t, J=6.2 Hz, 1H), 3.76 (m, 1H), 3.35-3.05 (m, 2H), 2.97 (m, 1H), 2.61 (m, 1H), 2.34 (m, 1H), 1.29 (br s, 9H)

(HPLC Analysis Condition)

column: YMC-Pack Pro C18 (YMC. Co., Ltd.), column size 4.6×150 mm, particle size 5 μm column temperature: 40° C.

mobile phase: A solution) 0.02M $K_2HPO_4$ (pH7.0): $CH_3CN$=70:30

B solution) 0.02M $K_2HPO_4$ (pH7.0): $CH_3CN$=30:70 gradient program:

TABLE 12

| Time (min) | Mobile Phase A (%) | Mobile Phase B (%) |
|---|---|---|
| 0:00 | 100 | 0 |
| 15:00 | 0 | 100 |
| 35:00 | 0 | 100 |
| 35:01 | 100 | 0 |
| 40:01 | 100 | 0 |

flow rate: 1.0 ml/min retention time:

compound (4a) 16.5 min compound (3) 7.7 min

DL-tartaric acid 1.4 min

Example 3

Synthesis of tert-butyl (2S,3S)-3-amino-2-[(3-bromo-2-fluorophenyl)methyl]pyrrolidine-1-carboxylate N-(4-methylbenzene-1-sulfonyl)-L-phenylalanine salt (N-(4-methylbenzene-1-sulfonyl)-L-phenylalanine salt of Compound (5a))

$Ru(OAc)_2$\{(R)-xylyl-binap\} (0.298 g), compound (4a) (23.24 g), ammonium chloride (13.36 g) and ammonium acetate (4.81 g) were charged to a autoclave. The mixture was subjected seven times to the operations of degassing under reduced pressure and restoring with nitrogen, under stirring. Methanol (232 ml) and water (2.87 ml) were charged to another reactor, and the mixture was subjected five times to the operations of degassing under reduced pressure and restoring with nitrogen, under stirring. The obtained degassed methanol-water solution was added to the pre-reaction mixture at 20° C. After stopping the stirring of the mixture, the mixture was subjected ten times to the operations of hydrogen pressurization to 0.10 MPa (G) and pressure release, at 20° C. After the hydrogen pressurization to 0.32 MPa (G) at 20° C., the stirring was resumed, and the mixture was heated to 80-85° C. The hydrogen pressure was adjusted to 0.90±0.05 MPa (G) at 80-85° C., and the mixture was stirred for 24 hr. The reaction solution was concentrated to 116 ml at the external temperature of 50° C. or lower. The concentrated solution was cooled to 25° C., and 1M aqueous sodium hydroxide solution (116 ml) and ethyl acetate (116 ml) were added thereto. The reaction solution was concentrated to 232 ml at the external temperature of 50° C. or lower. Ethyl acetate (116 ml) was added thereto, and the mixture was concentrated to 232 ml at the external temperature of 50° C. or lower. Ethyl acetate (116 ml) was added again thereto, and the mixture was concentrated to 232 ml at the external temperature of 50° C. or lower. Ethyl acetate (47 ml) was added thereto, and the mixture was allowed to stand at 25° C., and the aqueous layer was removed by separation. The obtained organic layer was concentrated to 70 ml at the external temperature of 50° C. or lower. Ethanol (116 ml) was added thereto, and the organic layer was concentrated to 70 ml at the external temperature of 50° C. or lower. Ethanol (116 ml) was added again to the concentrated solution, and the organic layer was concentrated to 70 ml at the external temperature of 50° C. or lower. Ethanol (163 ml) was added to the obtained concentrated solution, and the mixture was heated to 70° C. N-(4-Methylbenzene-1-sulfonyl)-L-phenylalanine (19.94 g) was added thereto at 70° C., the reactor used was washed with ethanol (23 ml), and the washing was added thereto. The mixture was stirred at 70° C. for 30 min, slowly cooled to 25° C., and stirred at 25° C. for 18 hr or longer. The crystals obtained by these operations were collected by filtration, washed with ethanol (186 ml), and dried under reduced pressure at 50° C. to give crystals (31.00 g) (99.1 HPLC area %) of the titled N-(4-methylbenzene-1-sulfonyl)-L-phenylalanine salt of compound (5a).

(Compound NMR Data)

$^1$H NMR (500 MHz, DMSO-$d_6$, observed as mixture of rotamers) δ7.63-7.45 (m, 3H), 7.30-6.94 (m, 9H), 4.07 (bs, 1H), 3.59 (t, J=6.0 Hz, 1H), 3.54-3.40 (m, 1H), 3.01-2.72 (m, 3H), 2.48-2.42 (m, 1H), 2.34 (s, 3H), 2.15-2.02 (m, 1H), 1.96-1.78 (m, 1H), 1.20 (s, 9H), 0.99.

(HPLC Analysis Condition)

column: YMC-Pack Pro C18 RS (YMC. Co., Ltd.), column size 4.6×150 mm, particle size 5 μm column temperature: 25° C.

mobile phase: A solution) 0.03M aqueous $K_2HPO_4$ solution

B solution) acetonitrile gradient program:

TABLE 13

| Time (min) | Mobile Phase A (%) | Mobile Phase B (%) |
|---|---|---|
| 0:00 | 90 | 10 |
| 2:00 | 90 | 10 |
| 15:00 | 30 | 70 |
| 30:00 | 30 | 70 |
| 33:00 | 90 | 10 |
| 40:00 | 90 | 10 |

flow rate: 1.0 ml/min retention time:

N-(4-methylbenzene-1-sulfonyl)-L-phenylalanine 9.77 min compound (5a) 15.02 min

Example 4

Synthesis of tert-butyl (2,3S)-2-[(3-bromo-2-fluorophenyl)methyl]-3-[(methanesulfonyl)amino]pyrrolidine-1-carboxylate (Compound (6a))

To N-(4-methylbenzene-1-sulfonyl)-L-phenylalanine salt of compound (5a) (60.0 g) was added toluene (600 ml), and the mixture was heated to 40 to 50° C. Aqueous sodium carbonate solution (900 ml) was added thereto, the mixture was stirred, and the pH of the solution was adjusted to 9 or more to dissolve N-(4-methylbenzene-1-sulfonyl)-L-phenylalanine salt of compound (5a). The solution was allowed to stand, and water (600 ml) was added to the separated organic layer. The mixture was stirred, and allowed again to stand, and the organic layer was separated. The obtained organic layer was concentrated to about 180 ml under reduced pressure at the external temperature of 50° C. or lower, toluene (300 ml) was added thereto, and the mixture was concentrated to 180 ml under reduced pressure. Ethyl acetate (420 ml) was added to the obtained concentrated solution at 20 to 30° C., and triethylamine (17.53 g) was added dropwise thereto at −2 to 8° C. The dropping funnel used was washed with ethyl acetate (30 ml), and the washing was added thereto. Methanesulfonyl chloride (13.89 g) was added dropwise thereto at −2 to 8° C., the dropping funnel used was washed with ethyl acetate (30 ml), and the washing was added thereto. The mixture was stirred at −2 to 8° C. for 1 hr, 0.5M hydrochloric acid (600 ml) was added dropwise thereto at 30° C. or lower, and the mixture was stirred for 15 min or longer, and allowed to stand. The organic layer was separated, 5% aqueous sodium hydrogencarbonate solution (600 ml) was added thereto, and the mixture was stirred at 20 to 30° C. for 15 min, and allowed to stand. The organic layer was separated, 5% aqueous sodium chloride solution (600 ml) was added thereto at 20 to 30° C., and the mixture was stirred, and allowed to stand, as in the previous step. The organic layer was separated, and concentrated to about 240 ml under reduced pressure at the external temperature of 50° C. or lower. The mixture was subjected twice to the operations of addition of toluene (240 ml) to the obtained concentrated solution, and concentration to about 240 ml under reduced pressure. Toluene (120 ml) was added thereto at 45 to 55° C., and n-heptane (120 ml) was added dropwise thereto over 30 min or longer at 45 to 55° C.

After confirmation of precipitation of crystals, the mixture was stirred at 45 to 55° C. for 2 hr or longer. n-Heptane (240 ml) was added dropwise thereto over 30 min or longer, and the mixture was stirred for 1 hr or longer, and then at 0 to 10° C. for 1 hr or longer. The precipitated crystals were collected by filtration, and washed with toluene/n-heptane (1:1) solution (120 ml) cooled to 0 to 10° C. and n-heptane-ethanol (10:1) solution (120 ml) cooled to 0 to 10° C. The crystals were dried under reduced pressure to give crystals (34.18 g) of the titled compound (6a).

(Compound NMR Data)

$^1$H NMR (300 MHz, DMSO-d6) δ7.61-7.53 (2H, m), 7.25-7.19 (1H, m), 7.09-7.04 (1H, m), 4.14-4.09 (1H, m), 3.94-3.84 (1H, m), 3.34-3.28 (2H, m), 3.01 (3H, s), 3.00-2.96 (1H, m), 2.44-2.36 (1H, m), 2.22-2.13 (1H, m), 2.03-1.89 (1H, m), 1.00 (9H, s).

(HPLC Analysis Condition)

column: L-column2 ODS (CERI, Japan), column size 4.6×100 mm, particle size 3 μm column temperature: constant temperature around 25° C.

mobile phase: A solution) 0.1% aqueous phosphoric acid solution

B solution) MeCN gradient program:

TABLE 14

| Time (min) | A Solution (%) | B Solution (%) |
|---|---|---|
| 0 | 80 | 20 |
| 10 | 20 | 80 |
| 15 | 20 | 80 |
| 16 | 80 | 20 |
| 25 | 80 | 20 |

flow rate: 1.0 ml/min retention time:

compound (6a) ca. 10 min compound (5a) ca. 5 min

Example 5

Synthesis of tert-butyl (2S,3S)-3-amino-2-[(3-bromo-2-fluorophenyl)methyl]pyrrolidine-1-carboxylate N-(4-methylbenzene-1-sulfonyl)-L-phenylalanine salt (N-(4-methylbenzene-1-sulfonyl)-L-phenylalanine salt of Compound (5a))

1) Synthesis of 2-[(3-bromo-2-fluorophenyl)methyl]pyrrolidin-3-one hemi-tartrate (hemi-tartrate of Compound (3))

tert-Butyl 3-oxopyrrolidine-1-carboxylate (compound (2a), 830 g) and toluene (4.8 L) were charged to a reactor, pyrrolidine (398 g) was added dropwise thereto at 40° C. or lower, and the mixture was stirred for 12 min. The reaction solution was concentrated to 3 L, toluene (3 L) was added to the concentrated solution, and the reaction solution was concentrated to 3 L. Again, toluene (3 L) was added to the concentrated solution, and the mixture was concentrated to 3 L. Acetonitrile (4.8 L) was added to the obtained concentrated solution, and tetrabutylammonium iodide (83 g) was added thereto. The temperature of the mixture was maintained at about 30° C., an acetonitrile solution (0.9 L) of 1-bromo-3-(bromomethyl)-2-fluorobenzene (compound (1), 600 g) was added dropwise thereto. The dropping funnel used was washed with acetonitrile (0.3 L), the washing was added thereto, and the mixture was stirred at 35-43° C. for 1 hr. Then, the mixture was cooled to 23° C., and the pH was adjusted to 2.8 with 2M hydrochloric acid. Ethyl acetate (4.8 L) was added thereto, the mixture was allowed to stand, and the aqueous layer was removed by separation to give an organic layer. 10% Aqueous sodium thiosulfate solution (4.2 L) was added to the obtained organic layer, and the mixture was allowed to stand, and the aqueous layer was removed by separation to give an organic layer. 10% Brine (4.2 L) was added to the obtained organic layer, and the mixture was allowed to stand, the aqueous layer was removed by separation, and the obtained organic layer was concentrated to 1.8 L.

2-Propanol (4.8 L) was added to the concentrated solution, and the mixture was concentrated to 1.8 L. Again, 2-propanol (4.8 L) was added to the concentrated solution, and the mixture was concentrated to 1.8 L. The concentrated solution was heated to 50° C., and while maintaining the temperature, 5M hydrogen chloride/2-propanol (1663 g) was added dropwise thereto to precipitate crystals. The mixture containing the precipitated crystals were stirred at 50° C. for 6 hr. Ethyl acetate (6.0 L) was slowly added thereto at 47-52° C., and the mixture was stirred at 52° C. for 1 hr. The mixture was slowly cooled to 1° C., and stirred at 1° C. for 1 hr, and the crystals were collected by filtration, and washed with ethyl acetate (1.8 L). Thus-obtained wet crystals of the hydrochloride of compound (3) and toluene (4.8 L) were charged to a reactor, and the mixture was cooled to 9° C. Triethylamine (272 g) was added dropwise thereto at 9 to 10° C. The mixture was stirred at 5° C. for 1.5 hr, and the insoluble substance was removed by filtration, and washed with toluene (3 L), and the washing was combined with the filtrate.

Methanol (6.0 L) and DL-tartaric acid (168 g) were charged to another reactor, and the mixture was stirred at 24° C. for 45 min. The above filtrate was added dropwise thereto over 2 hr or longer at 24° C. to precipitate crystals. The dropping funnel used was washed with toluene (0.6 L), and the washing was combined with the above mixture. The mixture was stirred at 25° C. for 1 hr, slowly cooled to 5° C. with stirring, and stirred at 0 to 5° C. for 12 hr. The precipitated crystals were collected by filtration, washed with toluene-methanol=2:1 solution (1.8 L) cooled to 5° C., and dried under reduced pressure to give crystals (425 g) (99.0 HPLC area %) of the titled hemi-tartrate of compound (3).

(Compound NMR Data)

$^1$H NMR (300 MHz, DMSO-$d_6$) δ=7.56 (t, J=7.3 Hz, 1H), 7.34 (t, J=7.3 Hz, 1H), 7.10 (t, J=7.3 Hz, 1H), 4.16 (m, 1H), 3.38 (dd, J=4.3, 9.3 Hz, 1H), 3.22 (m, 1H), 3.12-2.99 (m, 2H), 2.70 (dd, J=9.3, 14.2 Hz, 1H), 2.47-2.17 (m, 2H)

2) Synthesis of tert-butyl 2-[(3-bromo-2-fluorophenyl)methyl]-3-oxopyrrolidine-1-carboxylate (Compound (4a))

The hemi-tartrate of compound (3) (400 g) obtained in 1) and acetonitrile (2.4 L) were charged to a reactor, and triethylamine (257 g) was added dropwise thereto while maintaining the temperature at 20 to 21° C. $Boc_2O$ (251 g) and acetonitrile (0.6 L) were charged to another reactor, and the mixture was stirred at 25° C., and added dropwise to the above solution of compound (3). The dropping funnel used was washed with acetonitrile (0.2 L), and the washing was added to the reactor. Thus-obtained mixture was stirred at 23 to 28° C. for 1 hr. 10% Aqueous citric acid solution (2 L) and ethyl acetate (3.2 L) were added thereto, the mixture was stirred for 15 min, and allowed to stand for 45 min, and the aqueous layer was removed by separation. 5% Brine (2 L) was added to the obtained organic layer, the mixture was stirred for 15 min, and allowed to stand for 24 min, and the aqueous layer was removed by separation to give an organic layer. The obtained organic layer was passed through the three-connected Pall SUPRAcap 50 (Pall part no. SC050XAK2), and the filter was washed with a part of ethyl acetate (1.2 L). The insoluble substance was removed by filtration, and washed with the rest of the ethyl acetate (1.2 L), and the washing was combined with the filtrate. The filtrate was concentrated at the external temperature of 55-60° C. to adjust the volume to 1.2 L. Ethanol (4 L) was added thereto, and the mixture was concentrated to 1.2 L at the external temperature of 60° C. Ethanol (4 L) was added again to the concentrated solution, and the mixture was concentrated to 1.2 L at the external temperature of 60° C. Ethanol (0.8 L) was added to the concentrated solution at 25° C., and water (0.8 L) was added dropwise thereto at 26 to 27° C. The mixture was cooled to 8° C., and the seed crystals (218 mg) of compound (4a) were added thereto at 8° C. After confirmation of the crystallization, the mixture was stirred at 0 to 5° C. for 7.5 hr. Water (2 L) was added dropwise thereto, and the mixture was stirred at 0 to 5° C. for 12.5 hr. The crystals were collected by filtration, and washed with ethanol-water=1:2 (1.2 L) cooled to 0 to 6° C. The drained wet crystals were dried under reduced pressure at 25° C. or lower to give crystals (396 g) (99.2 HPLC area %) of the titled compound (4a). As the seed crystals for compound (4a), the crystals spontaneously precipitate prior to the addition of the seed crystals in the reaction described above were used.

(Compound NMR Data)

$^1$H NMR (300 MHz, DMSO-$d_6$) δ=7.58 (t, J=7.0 Hz, 1H), 7.20-7.04 (m, 2H), 4.12 (t, J=6.2 Hz, 1H), 3.76 (m, 1H), 3.35-3.05 (m, 2H), 2.97 (m, 1H), 2.61 (m, 1H), 2.34 (m, 1H), 1.29 (br s, 9H)

3) Synthesis of tert-butyl (2S,3S)-3-amino-2-[(3-bromo-2-fluorophenyl)methyl]pyrrolidine-1-carboxylate N-(4-methylbenzene-1-sulfonyl)-L-phenylalanine salt (N-(4-methylbenzene-1-sulfonyl)-L-phenylalanine salt of Compound (5a))

$Ru(OAc)_2${(R)-xylyl-binap} (3.2 g), the crystals (250 g) of compound (4a) obtained in 2), ammonium chloride (143.5 g), ammonium acetate (51.7 g), methanol (2.5 L) and water (125 ml) were charged to to an autoclave, and the mixture was subjected seven times to the operations of degassing under reduced pressure and restoring with nitrogen. After stopping the stirring of the mixture, the mixture was subjected ten times to the operations of hydrogen pressurization to 0.12 to 0.13 MPa (G) and pressure release. After the hydrogen pressurization to 0.32 MPa (G) at 20° C., the stirring was resumed, and the mixture was heated to 80-85° C. The hydrogen pressure was adjusted to 0.90±0.05 MPa (G) at 80-85° C., and the mixture was stirred for 40 hr. The reaction solution was concentrated to 1.25 L at the external temperature of 50° C. or lower. The concentrated solution was cooled to 25° C., 1M aqueous sodium hydroxide solution (1.25 L) and ethyl acetate (1.25 L) were added thereto. The reaction solution was concentrated to 2.5 L at the external temperature of 50° C. or lower. Ethyl acetate (1.25 L) was added to the concentrated solution, and the mixture was concentrated to 2.5 L at the external temperature of 50° C. or lower. Ethyl acetate (1.25 L) was added again to the obtained concentrated solution, and the mixture was concentrated to 1.25 L at the external temperature of 50° C. or lower. Ethyl acetate (0.5 L) was added thereto, the mixture was stirred for 15 min, and allowed to stand for 24 min, and the aqueous layer was removed by separation. The obtained organic layer was concentrated to 0.75 L at the external temperature of 50° C. or lower. Ethanol (1.25 L) was added thereto, and the organic layer was concentrated to 0.75 L at the external temperature of 50° C. or lower. Ethanol (1.25 L) was added again to the concentrated solution, and the organic layer was concentrated to 0.75 L at the external temperature of 50° C. or lower. Ethanol (1.75 L) was added to the obtained concentrated solution, and the mixture was heated to 68° C. N-(4-Methylbenzene-1-sulfonyl)-L-phenylalanine (214 g) was added thereto at 68 to 69° C., the reactor was washed with ethanol (0.25 L), and the washing was added to the mixture. The mixture was stirred at 75° C. for 30 min, slowly cooled to 22° C., and stirred at 22° C. for 18 hr. The crystals obtained by these operations were collected by filtration, washed with ethanol (186 ml), and dried under reduced pressure at 50° C. to give crystals (305 g) (99.6 HPLC area %) of the titled N-(4-methylbenzene-1-sulfonyl)-L-phenylalanine salt of compound (5a).

(Compound NMR Data)

$^1$H NMR (500 MHz, DMSO-$d_6$, observed as mixture of rotamers) δ7.63-7.45 (m, 3H), 7.30-6.94 (m, 9H), 4.07 (bs, 1H), 3.59 (t, J=6.0 Hz, 1H), 3.54-3.40 (m, 1H), 3.38-3.17 (m, 1H), 3.01-2.72 (m, 3H), 2.48-2.42 (m, 1H), 2.34 (s, 3H), 2.15-2.02 (m, 1H), 1.96-1.78 (m, 1H), 1.20 (s, 9H), 0.99.

(HPLC Analysis Condition)

column: YMC-Pack Pro C18 RS (YMC. Co., Ltd.), column size 4.6×150 mm, particle size 5 μm column temperature: 25° C.

mobile phase: A solution) 0.03M aqueous $K_2HPO_4$ solution

B solution) acetonitrile gradient program:

TABLE 15

| Time (min) | Mobile Phase A (%) | Mobile Phase B (%) |
|---|---|---|
| 0:00 | 90 | 10 |
| 2:00 | 90 | 10 |
| 15:00 | 30 | 70 |
| 30:00 | 30 | 70 |
| 33:00 | 90 | 10 |
| 40:00 | 90 | 10 |

flow rate: 1.0 ml/min retention time:

N-(4-methylbenzene-1-sulfonyl)-L-phenylalanine 9.77 min compound (5a) 15.02 min

The yield of thus-obtained N-(4-methylbenzene-1-sulfonyl)-L-phenylalanine salt of compound (5a) to compound (1) was about 33.1%.

Reference Example 1

Synthesis of tert-butyl (2S,3S)-3-[(methanesulfonyl) amino]-2-[(2,3',5'-trifluoro[1,1'-biphenyl]-3-yl) methyl]pyrrolidine-1-carboxylate (Compound (7a))

In a reactor, to 1,2-dimethoxyethane (225 ml), water (135 ml) and sodium hydroxide (3.99 g) were added the crystals (30 g) of compound (6a) and (3,5-difluorophenyl) boronic acid (12.6 g) at 25° C. 10% Pd carbon powder (PE-TYPE, manufactured by N.E. CHEMCAT) (179.3 mg) and Xphos (63.4 mg) were added thereto, and the mixture was subjected to degassing under reduced pressure and the reduced pressure was broken with nitrogen. The obtained mixture was stirred at 73 to 83° C. for 3 hr or longer, and ethyl acetate (330 ml) and water (270 ml) were added thereto at 45 to 55° C. The insoluble substance was removed by filtration at 25° C., and washed successively with ethyl acetate (60 ml) and water (60 ml). N-acetyl cysteine (5.42 g) and NaCl (19.5 g) were added to the filtrate at 25° C., and the mixture was stirred at 20 to 30° C. for 30 min or longer. Ethanol (300 ml) was added to the separated organic layer at 20 to 30° C., and the mixture was concentrated to about 450 ml under reduced pressure at the external temperature of 60° C. or lower. Then, the mixture was subjected twice to the operations of addition of ethanol (300 ml) with stirring at 40° C. or lower, and concentration to about 450 ml under reduced pressure at the external temperature of 60° C. or lower. Ethanol (150 ml) was added to the obtained concentrated solution at 40° C. or lower, and the mixture was heated to 60 to 65° C., and stirred for 30 min or longer. Water (600 ml) was added dropwise thereto at 60 to 65° C., and the mixture was stirred for 30 min or longer, and stirred at 20 to 30° C. for 1 hr or longer to precipitate crystals. The precipitated crystals were separated, washed with a mixed solvent (150 ml) of ethanol/water (1:1), and dried under reduced pressure at the external temperature of 60° C. to give crystals (31.40 g) of the titled compound (7a).

(Compound NMR Data)

$^1$H NMR (300 MHz, DMSO-$d_6$) δ7.61-7.59 (1H, m), 7.50-7.45 (1H, m), 7.33-7.20 (5H, m), 4.16-4.10 (1H, m), 3.95-3.85 (1H, m), 3.35-3.27 (2H, m), 3.01 (3H, s), 3.03-2.97 (1H, m), 2.50-2.44 (1H, m), 2.22-2.14 (1H, m), 2.05-1.91 (1H, m), 0.96 (9H, s).

(HPLC Analysis Condition)

column: L-column2 ODS (CERI, Japan), column size 4.6×100 mm, particle size 3 μm column temperature: constant temperature around 25° C.

mobile phase: A solution) 0.1% aqueous phosphoric acid solution

B solution) MeCN gradient program:

TABLE 16

| Time | Mobile Phase (v/v %) | | |
|---|---|---|---|
| (min) | A | B | Gradient conditions |
| 0 | 80 | 20 | Initial condition |
| 10 | 20 | 80 | Linear gradient |
| 15 | 20 | 80 | Isocratic region |
| 16 | 80 | 20 | Return to initial |
| 25 | 80 | 20 | Re-equilibration |

flow rate: 1.0 ml/min retention time:

compound (7a) ca. 10 min compound (6a) ca. 9 min

Reference Example 2

Synthesis of N-{(2S,3S)-2-[(2,3',5'-trifluoro[1,1'-biphenyl]-3-yl)methyl]pyrrolidin-3-yl}methanesulfonamide hydrochloride (hydrochloride of Compound (8))

To the crystals (5.00 g) of compound (7a) was added 2-propanol (55 ml), and 5-6M hydrogen chloride/2-propanol solution (6.2 ml) was added dropwise thereto with stirring at 15 to 35° C. The mixture was gradually heated to 65 to 75° C., and stirred for 2 hr or longer, and n-heptane (82.5 ml) was added dropwise thereto at 65 to 75° C. The mixture was gradually cooled to 5° C., and stirred for 2 hr or longer. The precipitated crystals were separated, washed with a mixed solvent (15 ml) of 2-propanol/n-heptane (1:2), and dried under reduced pressure at the external temperature of 50° C. to give crystals (4.15 g) of the titled hydrochloride of compound (8).

(Compound NMR Data)

$^1$H NMR (300 MHz, DMSO-$d_6$) δ9.38 (2H, brs), 7.60-7.49 (3H, m), 7.36-7.27 (4H, m), 4.19-4.11 (1H, m), 3.89-3.83 (1H, m), 3.47-3.37 (1H, m), 3.24-3.09 (3H, m), 3.01 (3H, s), 2.38-2.25 (1H, m), 2.10-2.00 (1H, m).

(HPLC Analysis Condition)

column: L-column2 ODS (CERI, Japan), column size 4.6×100 mm, particle size 3 μm column temperature: constant temperature around 25° C.

mobile phase: A solution) 0.1% aqueous phosphoric acid solution

B solution) MeCN gradient program:

TABLE 17

| Time | Mobile Phase (v/v %) | | |
|---|---|---|---|
| (min) | A | B | Gradient conditions |
| 0 | 80 | 20 | Initial condition |
| 10 | 20 | 80 | Linear gradient |
| 15 | 20 | 80 | Isocratic region |
| 16 | 80 | 20 | Return to initial |
| 25 | 80 | 20 | Re-equilibration |

flow rate: 1.0 ml/min retention time:

compound (8) ca. 5 min compound (7a) ca. 10 min (HPLC Analysis Condition)

column: YMC-Pack Pro C18 RS (YMC, Japan), column size 4.6×250 mm, particle size 5 μm column temperature: constant temperature around 25° C.

mobile phase: A solution) 0.1% aqueous phosphoric acid solution

B solution) MeCN gradient program:

TABLE 18

| Time | Mobile Phase (v/v %) | | |
|---|---|---|---|
| (min) | A | B | Gradient conditions |
| 0 | 95 | 5 | Initial condition |
| 2 | 95 | 5 | Isocratic region |

TABLE 18-continued

| Time (min) | Mobile Phase (v/v %) A | B | Gradient conditions |
|---|---|---|---|
| 30 | 30 | 70 | Linear gradient |
| 35 | 30 | 70 | Isocratic region |
| 38 | 95 | 5 | Return to initial |
| 50 | 95 | 5 | Re-equilibration |

flow rate: 1.0 ml/min
retention time: compound (8) ca. 17 min

Reference Example 3

Synthesis of N-{(2S,3S)-1-(2-hydroxy-2-methylpropanoyl)-2-[(2,3',5'-trifluoro[1,1'-biphenyl]-3-yl)methyl]pyrrolidin-3-yl}methanesulfonamide (Compound (I)) sesqui-hydrate Under nitrogen atmosphere, dimethylacetamide (30 ml) was charged to a reactor, 2-hydroxy-2-methylpropanoic acid (3.09 g) and 1,1-carbonyldiimidazole (CDI) (4.82 g) were added thereto at −10 to 0° C., the reactor was washed with dimethylacetamide (1.35 ml), and the washing was added to the mixture. Then, under nitrogen atmosphere, at −10 to 0° C., N-hydroxy-5-norbornene-2,3-dicarboxyimide (4.90 g) was added thereto, the reactor was washed with dimethylacetamide (1.35 ml), the washing was added to the mixture and the mixture was stirred for 2 hr or longer. The reactor was degassed under reduced pressure (the mixture was subjected to degassing under reduced pressure and the reduced pressure was broken with nitrogen) for three times. The crystals (5.00 g) of hydrochloride of compound (8) were added to the mixture under nitrogen atmosphere at −10 to 0° C., the reactor was washed with dimethylacetamide (1.35 ml), and the washing was added to the mixture. Triethylamine (4.45 g) was added dropwise thereto under nitrogen atmosphere at −10 to 0° C., the dropping funnel used was washed with dimethylacetamide (0.95 ml), and the washing was added to the mixture. The mixture was stirred under nitrogen atmosphere at 30 to 40° C. (target about 37° C.) for 4 hr or longer, and water (35 ml) was added dropwise thereto at 15 to 45° C. Sodium hydroxide was added thereto at 15 to 45° C. until the pH became 13.4 to 13.9, and the mixture was stirred at 40 to 60° C. for 1 hr or longer. The pH was adjusted to 7.5 to 8.5 with 6N hydrochloric acid at 20 to 40° C. The mixture was heated to 60° C., and water (the total amount of DMAc used×1.214−the amount of water used 2 vol−the amount of 6N hydrochloric acid used−the amount of aqueous NaOH solution and hydrochloric acid used for pH readjustment) was added dropwise thereto. The seed crystals (2.5 mg) of sesqui-hydrate of compound (I) were added thereto, and the mixture was stirred at 55 to 65° C. for 1 hr or longer. Water (10 ml) was added dropwise thereto at 55 to 65° C., and the mixture was cooled gradually to 45 to 55° C. over 30 min or longer, stirred for 1 hr or longer, cooled to 20 to 30° C. over 1.5 hr or longer, and stirred for 1 hr or longer. The precipitated crystals were separated, washed twice with a mixed solvent of ethanol (5 ml) and water (15 ml) to give a crude pre-reslurry-form of sesqui-hydrate of compound (I). Ethanol (12.5 ml), water (12.5 ml) and triethylamine (0.30 g) were charged to a reactor, and the obtained crude pre-reslurry-form of sesqui-hydrate of compound (I) was added thereto. The mixture was stirred at 40 to 50° C. for 30 min or longer, and water (25 ml) was added dropwise thereto over 20 min or longer at 40 to 50° C. Then, the mixture was stirred at 40 to 50° C. for 1 hr or longer, cooled to 20 to 30° C. over 1 hr or longer, and stirred for 1 hr or longer. The crystals were washed twice with a mixed solvent of ethanol (5 ml) and water (15 ml), drained, and dried under reduced pressure at the external temperature of 50° C. to give crude crystals (5.39 g) of sesqui-hydrate of compound (I).

Thus-obtained crude crystals (5 g) of sesqui-hydrate of compound (I), ethanol (40 ml) and purified water (5.0 ml) were charged to a reactor, and the mixture was stirred at 40° C. to give a solution. The solution was subjected to polish filtration, the filter was washed with ethanol (5.0 ml), and the washing was added to the filtrate. Purified water (40 ml) was added dropwise to the filtrate at 43 to 53° C., and the seed crystals (2.5 mg) of sesqui-hydrate of compound (I) was added thereto. After confirmation of precipitation of crystals, purified water (54 ml) was added dropwise thereto over 2 hr or longer at 48 to 53° C., and the mixture was stirred at 43 to 53° C. for 1 hr or longer, heated to 60 to 65° C., and stirred for 1 hr or longer. The mixture was cooled to 25° C. over 2 hr or longer, and stirred for 1 hr or longer. The crystals were separated, washed with a mixed solvent of ethanol (10 ml) and purified water (30 ml), dried under reduced pressure at the external temperature of 50° C., and subjected to humidification to give crystals (4.90 g) (purity 99.8%) of the title sesqui-hydrate of compound (I).

(Compound NMR Data)

$^1$H NMR (400 MHz, DMSO-$d_6$) δ7.51-7.21 (6H, m), 7.18-7.08 (1H, m), 5.00 (1H, s), 4.68-4.50 (1H, m), 3.99-3.69 (3H, m), 3.10-2.95 (1H, m), 2.95-2.85 (3H, m), 2.70-2.59 (1H, m), 2.23-2.11 (1H, m), 2.07-1.90 (1H, m), 1.19-1.04 (6H, m).

(HPLC Analysis Condition)

column: YMC-Pack Pro C18 (YMC. Co., Ltd.), column size 4.6×150 mm, particle size 5 μm column temperature: constant temperature around 25° C.

mobile phase: A solution) 0.01 mol/L phosphate buffer (pH3.0):MeCN=7:3

B solution) MeCN: 0.01 mol/L phosphate buffer (pH3.0)=4:1 gradient program:

TABLE 19

| Time (min) | A Solution (%) | B Solution (%) |
|---|---|---|
| 0 | 100 | 0 |
| 6 | 100 | 0 |
| 10 | 70 | 30 |
| 20 | 70 | 30 |
| 25 | 0 | 100 |
| 30 | 0 | 100 |
| 30.1 | 100 | 0 |
| 40 | 100 | 0 |

flow rate: 1.0 ml/min retention time: compound (I) ca. 17 min column: CHIRALPAK IE-3 (DAICEL), column size 4.6×150 mm, particle size 3 μm column temperature: constant temperature around 35° C.

mobile phase: A solution) 0.1% aqueous phosphoric acid solution:MeCN:THF=70:25:5 gradient program:

TABLE 20

| Time (min) | A Solution (%) |
|---|---|
| 0 | 100 |
| 30 | 100 |

flow rate: 1.0 ml/min
retention time:
compound (I) ca. 12 min
N-{(2R,3R)-1-(2-hydroxy-2-methylpropanoyl)-2-[(2,3',5'-trifluoro[1,1'-biphenyl]-3-yl)methyl]pyrrolidin-3-yl}methanesulfonamide (enantiomer of compound (I)) ca. 14 min

INDUSTRIAL APPLICABILITY

According to the production method of the present invention, compound (5) can be obtained as N-(4-methylbenzene-1-sulfonyl)-L-phenylalanine salt by a method suitable for industrial production.

The invention claimed is:

1. A method for producing a salt of formula (V)

(V)

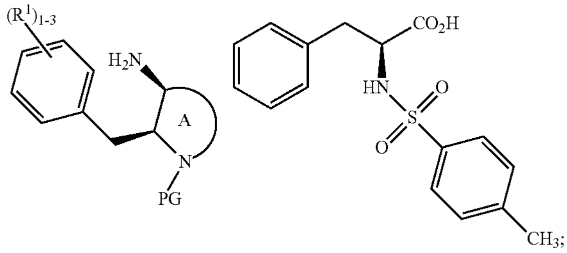

wherein each $R^1$ is independently selected from a halogen atom and a trifluoromethanesulfonyl group;

A is an optionally further substituted 4-7 membered N-containing monocyclic saturated heterocyclyl; and PG is a protecting group, the process comprising subjecting a compound of formula (IV):

(IV)

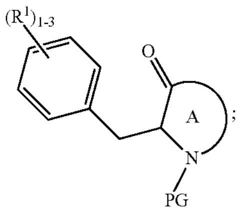

to an asymmetric reductive amination reaction in the presence of a metal complex comprising a chiral ligand and subjecting the resulting product to purification using salt formation with N-(4-methylbenzene-1-sulfonyl)-L-phenylalanine.

2. The method of claim 1, further comprising:

(a) reacting a compound of formula (II):

(II)

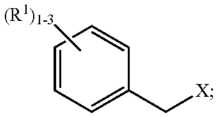

wherein $R^1$ is independently selected from a halogen atom and a trifluoromethanesulfonyl group; and X is a halogen atom, with an anion of a compound of formula (III):

III)

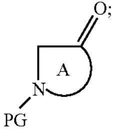

wherein

PG is a protecting group; and

A is an optionally further substituted 4-7 membered N-containing monocyclic saturated heterocycle;

(b) deprotecting the product of step (a);

(c) reacting the product of step (b) with a racemate of an organic acid; and (d) introducing a protecting group to the product of step (c);

to provide the compound of formula (IV).

3. The method of claim 1, wherein A is selected from pyrrolidine, piperidine, and azetidine, each of which is optionally further substituted.

4. The method of claims 1, wherein each $R^1$ is independently selected from Cl, Br, I, and a trifluoromethanesulfonyl group.

5. The method of claim 2, wherein the organic acid is racemic tartaric acid (DL-tartaric acid).

6. A method for producing N-(4-methylbenzene-1-sulfonyl)-L-phenylalanine salt of (2S,3S)-2-[(3-bromo-2-fluorophenyl) methyl]pyrrolidin-3-amine with a protecting group at the 1-position on the pyrrolidine, which comprises a step comprising Step 3a: subjecting 2-[(3-bromo-2-fluorophenyl) methyl] pyrrolidin-3-one with a protecting group at the 1-position on the pyrrolidine to an asymmetric reductive amination reaction in the presence of a metal complex comprising a chiral ligand; and Step 3b: subjecting the product of Step 3a to purification using salt formation with N-(4-methylbenzene-1-sulfonyl)-L-phenylalanine.

7. The method of claim 6, further comprising

Step 1a: reacting 1-bromo-3-(bromomethyl)-2-fluorobenzene and pyrrolidin-3-one with a protecting group at the 1-position on the pyrrolidine;

Step 1b: deprotecting the product of Step 1a and reacting with DL-tartaric acid; and Step 2: introducing a protecting group to the product of Step 1b to provide 2-[(3-bromo-2-fluorophenyl) methyl] pyrrolidin-3-one with a protecting group at the 1-position on the pyrrolidine.

8. The method according to claim 1, wherein the chiral ligand in the metal complex is a BINAP ligand, a phosphine ligand, a ferrocene ligand, or a cyclophane ligand.

9. The method according to claim 1, wherein the metal in the metal complex is ruthenium, rhodium, or iridium.

10. The method according to claim 1, wherein the metal complex comprising a chiral ligand is a ruthenium complex comprising a chiral BINAP ligand, or a ruthenium complex comprising a chiral cyclophane ligand.

11. The method according to claim 1, wherein the metal complex comprising a chiral ligand is a metal complex represented by the formula:

$$Ru(OAc)_2(Ligand)$$

wherein Ligand is (S)-binap, (R)-xylyl-Phanephos or (R)-xylyl-binap.

12. The method according to claim 1, wherein the metal complex comprising a chiral ligand is $Ru(OAc)_2$\{(R)-xylyl-binap\}.

13. The method according to claim 1, wherein the protecting group is selected from tert-butoxycarbonyl, benzyloxycarbonyl, acetyl, trityl, benzyl, 9-fluorenylmethyloxycarbonyl, 2,2,2-trichloroethoxycarbonyl, and methoxymethyl.

14. The method according to claim 1, wherein the protecting group is tert-butoxycarbonyl.

15. The method according to claim 1, wherein the purification conditions comprises recrystallization.

16. The method according to claim 15, wherein the crystallization comprises a salt formation with N-(4-methylbenzene-1-sulfonyl)-L-phenylalanine, which is conducted in a solvent at a temperature from 60° C. to 78° C., stirring at a temperature from 60° C. to 78° C., for about 0.5 hours, stirring at 15° C. to 35° C. for about 12 to about 48 hours, and filtering the resulting precipitate.

17. The method according to claim 16, further comprising recrystallizing the precipitate from a solvent selected from an alcohol, ether, or aromatic hydrocarbon.

18. The method according to claim 17, wherein the solvent is ethanol.

19. The method according to claim 6, further comprising:

Step 4: subjecting the N-(4-methylbenzene-1-sulfonyl)-L-phenylalanine salt of (2S,3S)-2-[(3-bromo-2-fluorophenyl) methyl]pyrrolidin-3-amine with a protecting group at the 1-position on the pyrrolidine to desalination and reacting with a methanesulfonylating agent;

Step 5: reacting the product of Step 4 with (3,5-difluorophenyl) boronic acid;

Step 6: subjecting the product of Step 5 to deprotection conditions; and

Step 7: subjecting the product of Step 6 to a condensation reaction with 2-hydroxy-2-methylpropanoic acid to give N-\{(2S,3S)-1-(2-hydroxy-2-methylpropanoyl)-2-[(2,3',5'-trifluoro [1,1'-biphenyl]-3-yl)methyl]pyrrolidin-3-yl\} methanesulfonamide, or a hydrate thereof, or a solvate thereof.

20. A compound which is a racemic organic acid salt of

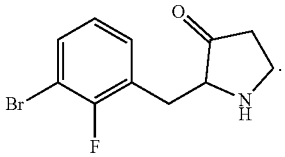 [SMILES: O=C1CCNC1Cc1cccc(Br)c1F].

21. The compound of claim 20, which is a racemic tartaric acid salt.

22. The compound of claim 20, which is

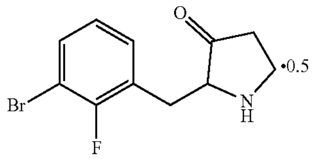
•0.5 tartaric acid.

* * * * *